(12) United States Patent
Suda et al.

(10) Patent No.: US 8,304,427 B2
(45) Date of Patent: Nov. 6, 2012

(54) ACYLTHIOUREA COMPOUND OR SALT THEREOF, AND USE THEREOF

(75) Inventors: Yoshimitsu Suda, Hanno (JP); Kosuke Egami, Hanno (JP); Hidenori Fujita, Hanno (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 246 days.

(21) Appl. No.: 12/937,312

(22) PCT Filed: Apr. 9, 2009

(86) PCT No.: PCT/JP2009/001655
§ 371 (c)(1),
(2), (4) Date: Oct. 11, 2010

(87) PCT Pub. No.: WO2009/125597
PCT Pub. Date: Oct. 15, 2009

(65) Prior Publication Data
US 2011/0034439 A1 Feb. 10, 2011

(30) Foreign Application Priority Data
Apr. 10, 2008 (JP) .................. 2008-102832

(51) Int. Cl.
*A61K 31/04* (2006.01)
*C07D 215/38* (2006.01)
(52) U.S. Cl. ...................... 514/312; 546/159
(58) Field of Classification Search .............. 514/312; 546/159
See application file for complete search history.

(56) References Cited

U.S. PATENT DOCUMENTS

| 7,135,466 B2 | 11/2006 | Sakai et al. |
| 7,253,286 B2 | 8/2007 | Funahashi et al. |
| 7,425,564 B2 | 9/2008 | Fujiwara et al. |
| 7,579,473 B2 | 8/2009 | Bannen et al. |
| 2006/0160832 A1 | 7/2006 | Funahashi et al. |
| 2006/0247259 A1 | 11/2006 | Funahashi et al. |
| 2008/0161305 A1 | 7/2008 | Forsyth et al. |

FOREIGN PATENT DOCUMENTS

| EP | 1 411 046 A1 | 4/2004 |
| JP | 2005 272474 | 10/2005 |
| WO | 01 047890 | 7/2001 |
| WO | 03 000660 | 1/2003 |
| WO | 2005 030140 | 4/2005 |
| WO | 2005 121125 | 12/2005 |
| WO | 2006 104161 | 10/2006 |
| WO | 2006 108059 | 10/2006 |

OTHER PUBLICATIONS

Hernandez, Synthesis, vol. 3, Nos. 3-4, pp. 299-316, 2005.*
Rao, Med Chem Res, Voi 20:333-338, 2011.*

International Search Report issued May 19, 2009 in PCT/JP09/01655 filed Apr. 9, 2009.
Christensen, G. James et al., "c-Met as a target for human cancer and characterization of inhibitors for therapeutic intervention", Cancer Letters, vol. 225, pp. 1-26, (2005).
Weidner, K. Michael et al., "Scatter Factor: Molecular Characteristics and Effect on the Invasiveness of Epithelial Cells", The Journal of Cell Biology, vol. 111, pp. 2097-2108, (Nov. 1990).
Comoglio, M. Paolo et al., "Scatter factors and invasive growth", Cancer Biology, vol. 11, pp. 153-165, (2001).
Xin, Xiaohua et al., "Hepatocyte Growth Factor Enhances Vascular Endothlial Growth Factor-Induced Angiogenesis in Vitro and in Vivo", American Journal of Pathology, vol. 158, No. 3, pp. 1111-1120, (Mar. 2001).
Ichimura, Eiji et al., "Expression of c-met/HGF Receptor in Human Non-small Cell Lung Carcinomas in vitro and in vivo and Its Prognostic Significance", Jpn J. Cancer Res, vol. 87, pp. 1063-1069, (Oct. 1996).
Nakajima, Masakazu et al., "The Prognostic Significance of Amplification and Overexpression of c-met and c-erb B-2 in Human Gastric Carcinomas", Cancer, vol. 85, No. 9, pp. 1894-1902, (May 1, 1999).
Extended European Search Report issued Apr. 11, 2012, in European Patent Application No. 09730440.6.

* cited by examiner

*Primary Examiner* — D M Seaman
(74) *Attorney, Agent, or Firm* — Oblon, Spivak, McClelland, Maier & Neustadt, L.L.P.

(57) ABSTRACT

Provided is a c-Met inhibitory antitumor agent which mitigates side effects by selectively affecting tumor cells in which c-Met is specifically expressed, having a formula (I) or its salt:

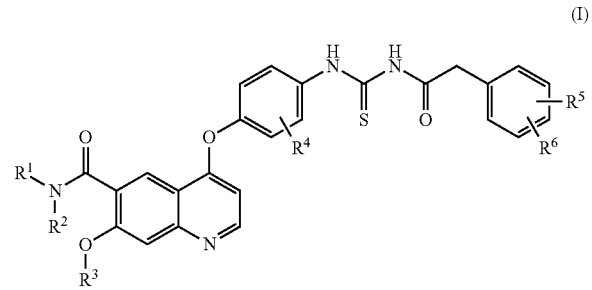

(I)

wherein each of $R^1$ and $R^2$ are independently a hydrogen atom, an optionally substituted $C_{1-6}$ alkyl, $C_{3-10}$ cycloalkyl, $C_{6-14}$ aromatic hydrocarbon, or saturated or unsaturated heterocyclic group, or $R^1$ and $R^2$ may form, together with the nitrogen atom to which they are attached, an optionally substituted nitrogen-containing heterocyclic ring; $R^3$ is a $C_{1-6}$ alkyl group; and $R^4$, $R^5$, and $R^6$, are independently a hydrogen atom, a halogen atom, an optionally substituted $C_{1-6}$ alkyl group, a $C_{1-6}$ alkoxy group, a $C_{1-6}$ alkylamino group, an optionally substituted aromatic hydrocarbon group, or an optionally substituted saturated or unsaturated heterocyclic group, or $R^5$ and $R^6$ may form a ring together with the phenyl ring to which they are attached.

12 Claims, 1 Drawing Sheet

ACYLTHIOUREA COMPOUND OR SALT THEREOF, AND USE THEREOF

CROSS REFERENCE TO RELATED APPLICATIONS

The present application is the national stage of international application PCT/JP2009/001655, filed on Apr. 9, 2009, and claims the benefit of the filing date of Japanese Application No. 2008-102832, filed on Apr. 10, 2008.

FIELD OF THE INVENTION

The present invention relates to a novel acylthiourea compound or a salt thereof, and to use thereof.

BACKGROUND OF THE INVENTION

The enzyme c-Met is a receptor tyrosine kinase identified as a proto-oncogene and exhibits its physiological function when bound to HGF serving as a ligand. In normal tissues, c-Met plays a role in regeneration, wound healing, and organ formation. However, in many cancer cells (kidney cell cancer, stomach cancer, lung cancer, colorectal cancer, pancreatic cancer, ovarian cancer, liver cell cancer, head and neck cancer, melanoma, etc.), occurrence of over-expression, mutation, or translocation of c-Met is promoted, leading to an excessively activated state (Non-Patent Document 1). Under such conditions, c-Met plays a role in cell proliferation, infiltration/metastasis, tumorigenesis, neovascularization, and anti-apoptosis (see, Non-Patent Documents 2, 3, and 4). In addition, many studies have revealed that over-expression and elevation in activation level of c-Met in cancer cells are negatively correlated to prognosis, and c-Met is known to be a factor associated with a poor prognosis of cancer (see Non-Patent Documents 5 and 6).

Therefore, if a drug which specifically inhibits c-Met in cancer/tumor cells in which c-Met is activated through over-expression is administered, proliferation, infiltration, and metastasis of cancer cells would be inhibited more specifically and intensively, whereby the drug is expected to contribute to the treatment of cancer, prolongation of the life of patients, and enhancement in QOL. Meanwhile, in actual therapy, since the expression level and activation level of c-Met serve as indices for stratification of patients, the patients can receive appropriate therapy, which is highly preferred from an ethical viewpoint.

Hitherto, there has been widely studied use of acylthiourea compounds as pharmaceutical agents or other agents (see, for example, Patent Documents 1 to 7). However, there has never been reported the acylthiourea compound of the present invention represented by formula (I), the compound having an aminocarbonyl group serving as a 6-position substituent of the quinoline ring and an alkoxy group serving as a 7-position substituent of the quinoline ring.

RELATED ART DOCUMENTS

Non-Patent Documents

Non-Patent Document 1: Cancer Letters, 225, p. 1-26 (2005)
Non-Patent Document 2: J. Cell Biol. 111, p. 2097-2108 (1990)
Non-Patent Document 3: Semin Cancer Biol, 11, p. 153-165 (2001)
Non-Patent Document 4: Am. J. Pathol., 158, p. 1111-1120 (2001)
Non-Patent Document 5: Jpn. J. Cancer Res., 87, p. 1063-1069 (1996)
Non-Patent Document 6: Cancer, 85 (9), p. 1894-1902 (1999)

Patent Documents

Patent Document 1: WO 2001/047890
Patent Document 2: WO 2002/032872
Patent Document 3: WO 2003/000660
Patent Document 4: WO 2005/030140
Patent Document 5: WO 2005/121125
Patent Document 6: WO 2006/104161
Patent Document 7: WO 2006/108059

SUMMARY OF THE INVENTION

Problems to be Solved by the Invention

An object of the present invention is to provide an antitumor agent which exhibits excellent c-Met inhibitory effect and which mitigates side effects by virtue of selectively damaging to tumor cells in which c-Met is specifically expressed.

Means for Solving the Problems

The present inventors have carried out extensive studies in order to solve the aforementioned problem, and have found that, as compared with conventional compounds which have a c-Met inhibitory effect, an acylthiourea compound of the present invention represented by formula (I), the compound having an aminocarbonyl group serving as a 6-position substituent of the quinoline ring and an alkoxy group serving as a 7-position substituent of the quinoline ring, (1) has a c-Met inhibitory effect equivalent to or higher than that of the conventional compounds in in vitro studies, (2) exhibits higher selective damage to tumor cells in which c-Met is over-expressed or highly activated, as compared with tumor cells in which c-Met is expressed at low level and normal cells, and (3) mitigates side effects and exhibits potent tumor-regression in in vivo studies using xenograft models. In other words, the inventors have found that the acylthiourea compound represented by formula (I), which selectively acts on tumor cells in which c-Met is specifically expressed, mitigates side effects and is useful as an excellent antitumor agent. The present invention has been accomplished on the basis of this finding.

Accordingly, the present invention provides an acylthiourea compound represented by formula (I):

[F1]

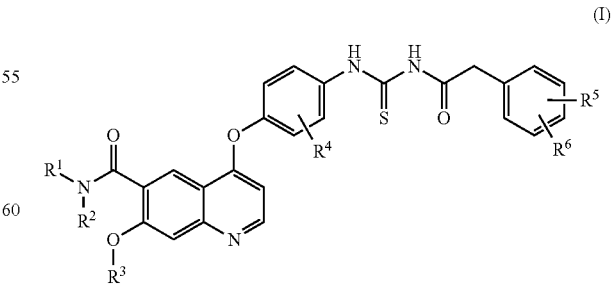

(I)

(wherein each of $R^1$ and $R^2$, which may be the same or different, represents a hydrogen atom, an optionally substituted $C_{1-6}$ alkyl group, an optionally substituted $C_{3-10}$ cycloalkyl group, an optionally substituted $C_{6-14}$ aromatic hydrocarbon group, or an optionally substituted saturated or unsaturated heterocyclic group, or $R^1$ and $R^2$ may form, together with the nitrogen atom to which they are attached, an optionally substituted nitrogen-containing heterocyclic ring;

$R^3$ represents a $C_{1-6}$ alkyl group; and each of $R^4$, $R^5$, and $R^6$, which may be identical to or different from one another, represents a hydrogen atom, a halogen atom, an optionally substituted $C_{1-6}$ alkyl group, a $C_{1-6}$ alkoxy group, a $C_{1-6}$ alkylamino group, an optionally substituted aromatic hydrocarbon group, or an optionally substituted saturated or unsaturated heterocyclic group, or $R^5$ and $R^6$ may form a ring together with the phenyl ring to which they are attached) or a salt thereof.

The present invention also provides a pharmaceutical agent containing, as an active ingredient, an acylthiourea compound represented by formula (I) or a salt thereof.

The present invention also provides a pharmaceutical composition comprising an acylthiourea compound represented by formula (I) or a salt thereof, and a pharmaceutically acceptable carrier.

The present invention also provides use of an acylthiourea compound represented by formula (I) or a salt thereof for producing an antitumor agent.

The present invention also provides a method for treating cancer, comprising administering, to a subject in need thereof, an effective amount of an acylthiourea compound represented by formula (I) or a salt thereof.

Effects of the Invention

Patent Document 6 discloses a compound similar to the compound of the present invention, the disclosed compound having a quinoline ring and an acylthiourea structure. However, Patent Document 6 discloses no such a compound having an aminocarbonyl group as a 6-position substituent of the quinoline ring, which substituent is a characteristic feature of the present invention. As shown in the Test Examples described hereinbelow, the compound of the present invention, characterized by having an aminocarbonyl group as a 6-position substituent of the quinoline ring, exhibits in in vitro tests an inhibitory activity to c-Met kinase equivalent to or higher than that of the similar compound disclosed in Patent Document 6 (comparative compound 1). However, quite surprisingly, when administered at a dose at which comparative compound 1 would be toxic, the compound of the present invention exhibited no toxicity (i.e., loss of body weight). Therefore, the dose of the compound can be increased, and a potent tumor reducing effect was observed in nude mice subjected to in vivo tests.

As described above, the compound (I) of the present invention or a salt thereof has an excellent c-Met inhibitory action in in vitro tests, the c-Met inhibitory action having high selectivity to tumor cells in which c-Met is specifically expressed, and exhibits potent tumor reducing effect in in vivo tests. Thus, the compound of the invention is a useful antitumor agent mitigating side effects.

Diseases treated through administration of a drug containing the compound of the present invention include, for example, malignant tumors such as head and neck cancer, esophageal cancer, stomach cancer, colon cancer, rectal cancer, liver cancer, gallbladder/bile duct cancer, biliary tract cancer, pancreatic cancer, lung cancer, breast cancer, ovarian cancer, cervical cancer, uterine cancer, kidney cancer, bladder cancer, prostate cancer, testicular tumor, bone and soft tissue sarcoma, leukemia, malignant lymphoma, multiple myeloma, skin cancer, brain tumor, and mesothelioma. In addition, the compound of the invention is particularly effective for treatment of proliferative diseases involving differentiation induction and proliferation of cells (e.g., proliferative and immunologic malignant skin diseases involving cornification or inflammation such as psoriasis); is useful as immunosuppressor in the treatment of immunologic diseases such as rheumatism; and in transplant of organs.

DETAILED DESCRIPTION OF THE INVENTION

Figure 1:
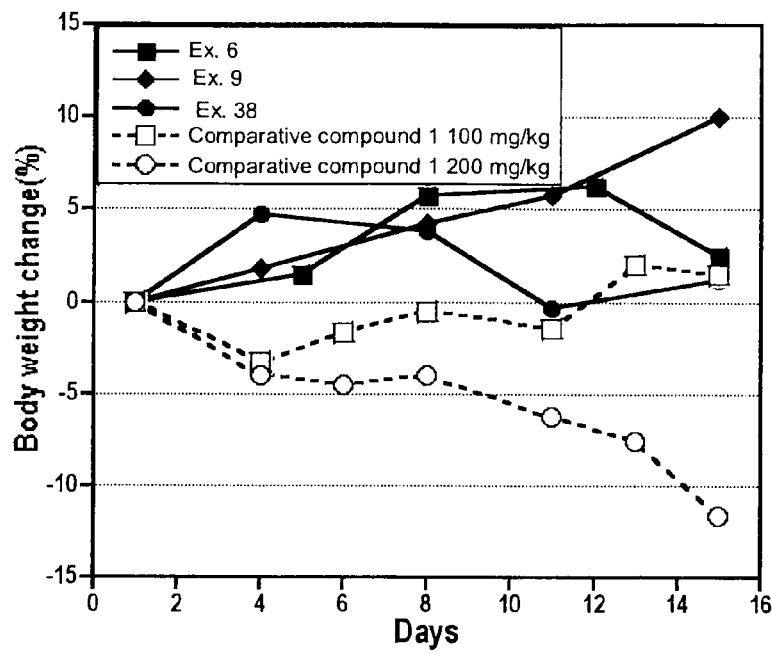
FIG. 1 A graph showing effects of the compounds of the present invention and those of comparative compounds, on the body weight of mice.

In the present invention, when the expression "optionally substituted" has been added to structural information, it refers to that the relevant structure may have one or more substituents at a chemically substitutable position(s).

The type, number, and locant of the substituent(s) present in the structure are not particularly limited. When two or more substituents are present, they may be identical to or different from one another. Examples of the "substituent" include a halogen atom, a hydroxyl group, a cyano group, a nitro group, a $C_{1-6}$ alkanoyl group, a $C_{1-6}$ alkyl group, a $C_{3-10}$ cycloalkyl group, a $C_{2-6}$ alkenyl group, a $C_{1-6}$ alkoxy group, an amino group, a $C_{1-6}$ alkylamino group, a $C_{1-6}$ alkanoylamino group, a $C_{1-6}$ alkylaminocarbonyl group, a $C_{1-6}$ alkylsulfonyl group, a $C_{6-14}$ aromatic hydrocarbon group, a saturated or unsaturated heterocyclic group, a saturated or unsaturated heterocyclic-carbonyl group, and an oxo group. When the substituent(s) is or are present, the number thereof is typically 1 to 3.

In formula (I), the "$C_{1-6}$ alkyl group" in the "optionally substituted $C_{1-6}$ alkyl group" represented as $R^1$ or $R^2$ is a C1 to C6 linear or branched alkyl group. Examples of the alkyl group include methyl, ethyl, n-propyl, isopropyl, n-butyl, sec-butyl, tert-butyl, n-pentyl, isopentyl, n-hexyl, and isohexyl group.

In formula (I), the "$C_{3-10}$ cycloalkyl group" in the "optionally substituted $C_{3-10}$ cycloalkyl group" represented as $R^1$ or $R^2$ is a C3 to C10 cycloalkyl group. Examples include cyclopropyl, cyclobutyl, cyclopentyl, and cyclohexyl group.

In formula (I), the "$C_{6-14}$ aromatic hydrocarbon group" in the "optionally substituted $C_{6-14}$ aromatic hydrocarbon group" represented as $R^1$ or $R^2$ is a C6 to C14 aromatic hydrocarbon group. Examples include phenyl and naphthyl group.

In formula (I), the "saturated or unsaturated heterocyclic group" in the "optionally substituted saturated or unsaturated heterocyclic group" represented as $R^1$ or $R^2$ is a monocyclic or bicyclic saturated or unsaturated heterocyclic group having one or two atoms selected from an oxygen atom, a nitrogen atom, and a sulfur atom. Examples include pyrrolidinyl, piperidinyl, piperazinyl, morpholino, thiomorpholino, homopiperidinyl, tetrahydrothienyl, imidazolyl, thienyl, furyl, pyrrolyl, oxazolyl, isoxazolyl, thiazolyl, isothiazolyl, pyrazolinyl, triazolyl, tetrazolyl, pyridyl, pyrazyl, pyrimidinyl, pyridazyl, indolyl, isoindolyl, indazolyl, methylenedioxyphenyl, ethylenedioxyphenyl, benzofuranyl, dihydrobenzofuranyl, benzoimidazolyl, benzoxazole, benzothiazolyl, purinyl, quinolyl, isoquinolyl, quinazolinyl, and quinoxalyl group. Among them, 5- to 7-membered saturated heterocycles each having one or two nitrogen atoms; e.g., pyrrolidinyl, piperidinyl, piperazinyl, homopiperidinyl, and tetrahydrothienyl groups, are preferred.

In formula (I), examples of the "nitrogen-containing heterocyclic ring" in the "optionally substituted nitrogen-containing heterocyclic ring" formed from $R^1$ and $R^2$ together with the nitrogen atom to which they are attached include nitrogen-containing saturated heterocyclic groups such as pyrrolidinyl, piperidinyl, piperazinyl, and morpholino group. Of these, pyrrolidinyl and piperidinyl groups are preferred.

In formula (I), examples of the "$C_{1-6}$ alkyl group" represented as $R^3$ include the aforementioned alkyl groups. Of these, $C_{1-3}$ alkyl group are preferred, with methyl group being more preferred.

In formula (I), examples of the halogen atom represented as $R^4$, $R^5$, or $R^6$ include a fluorine atom, a bromine atom, a chlorine atom, and an iodine atom. Of these, a fluorine atom and a chlorine atom are preferred.

In formula (I), the "$C_{1-6}$ alkyl group" in the "optionally substituted $C_{1-6}$ alkyl group" represented as $R^4$, $R^5$, or $R^6$ include the aforementioned alkyl groups. Of these, methyl group is preferred.

In formula (I), the "$C_{1-6}$ alkoxy group" in the "optionally substituted $C_{1-6}$ alkoxy group" represented as $R^4$, $R^5$, or $R^6$ is a C1 to C6 linear or branched alkoxy group. Examples include methoxy, ethoxy, n-propyloxy, isopropyloxy, n-butyloxy, sec-butyloxy, tert-butyloxy, n-pentyloxy, and n-hexyloxy group. Of these, $C_{1-3}$ alkoxy groups are preferred, with methoxy group being more preferred.

In formula (I), the "$C_{1-6}$ alkylamino group" in the "optionally substituted $C_{1-6}$ alkylamino group" represented as $R^4$, $R^5$, or $R^6$ is an amino group mono- or di-substituted with the aforementioned $C_{1-6}$ alkyl group. Examples include methylamino, ethylamino, dimethylamino, methylethylamino, n-propylamino, isopropylamino, n-butylamino, sec-butylamino, tert-butylamino, n-pentylamino, and n-hexylamino group.

In formula (I), the "aromatic hydrocarbon group" in the "optionally substituted aromatic hydrocarbon group" represented as $R^4$, $R^5$, or $R^6$ is the aforementioned C6 to C14 aromatic hydrocarbon group. Examples of preferred members include phenyl and naphthyl group.

In formula (I), the "saturated or unsaturated heterocycle" in the "optionally substituted saturated or unsaturated heterocycle" represented as $R^4$, $R^5$, or $R^6$ include the aforementioned saturated or unsaturated heterocyclic groups. Examples of preferred members include 5- to 7-membered saturated heterocyles each having one or two nitrogen atoms such as pyrrolidinyl, piperidinyl, and piperazinyl group.

Examples of the ring formed together with the phenyl ring to which $R^5$ and $R^6$ are attached include a naphthalene ring, a quinoline ring, a quinazoline ring, an indole ring, a benzimidazole ring, a methylenedioxyphenyl ring, and an ethylenedioxyphenyl ring.

Details of the aforementioned substituents are described as below. Examples of the halogen atom include the aforementioned halogen atoms. Examples of the $C_{1-6}$ alkanoyl group include formyl, acetyl, propionyl, and butylyl group. Examples of the $C_{1-6}$ alkyl group include the aforementioned $C_{1-6}$ alkyl groups. Examples of the $C_{3-10}$ cycloalkyl group include the aforementioned $C_{3-10}$ cycloalkyl groups. Examples of the $C_{2-6}$ alkenyl group include vinyl and 2-propenyl group. Examples of the $C_{1-6}$ alkoxy group include the aforementioned $C_{1-6}$ alkoxy groups. Examples of the $C_{1-6}$ alkylamino group include the aforementioned $C_{1-6}$ alkylamino groups. Examples of the $C_{1-6}$ alkanoylamino group include amino groups each substituted with the aforementioned $C_{1-6}$ alkanoyl group. Examples of the $C_{1-6}$ alkylaminocarbonyl group include aminocarbonyl groups each mono- or di-substituted with the aforementioned $C_{1-6}$ alkyl group. Examples of the $C_{1-6}$ alkylsulfonyl group include sulfonyl groups each substituted with the aforementioned $C_{1-6}$ alkyl group. Examples of the $C_{6-14}$ aromatic hydrocarbon group include the aforementioned $C_{6-14}$ aromatic hydrocarbon groups. Examples of the saturated or unsaturated heterocyclic group include the aforementioned saturated or unsaturated heterocyclic group.

$R^1$ is preferably a hydrogen atom or a $C_{1-3}$ alkyl group, with a hydrogen atom and methyl being more preferred. Among them, a hydrogen atom is particularly preferred.

$R^2$ is preferably an optionally substituted $C_{1-6}$ alkyl group, an optionally substituted $C_{6-14}$ aromatic hydrocarbon group, or an optionally substituted saturated or unsaturated heterocyclic group.

The $C_{1-6}$ alkyl group represented as $R^2$ is more preferably a $C_{1-4}$ alkyl group, with methyl, ethyl, n-propyl, isopropyl, n-butyl, and sec-butyl groups being particularly preferred. Now, the substituent of the $C_{1-6}$ alkyl group represented as $R^2$ will be described in detail. The substituent is preferably selected from among a hydroxyl group, a $C_{3-10}$ cycloalkyl group, a $C_{1-6}$ alkoxy group, a $C_{1-6}$ alkylamino group, a $C_{1-6}$ alkanoylamino group, a $C_{1-6}$ alkylsulfonyl group, an aromatic hydrocarbon group, a saturated or unsaturated heterocyclic group, a $C_{1-6}$ alkylaminocarbonyl group, and a saturated or unsaturated heterocyclic-carbonyl group. The $C_{3-10}$ cycloalkyl group is more preferably cyclohexyl group. The $C_{1-6}$ alkoxy group is more preferably a $C_{1-3}$ alkoxy group, with methoxy, ethoxy, and isopropyloxy groups being particularly preferred. The $C_{1-6}$ alkoxy group may further have a substituent. Such a substituent is preferably a hydroxyl group. The $C_{1-6}$ alkylamino group is more preferably a diethylamino group. The $C_{1-6}$ alkanoylamino group is more preferably an acetylamino group. The $C_{1-6}$ alkylsulfonyl group is more preferably a methylsulfonyl group. The aromatic hydrocarbon group is more preferably phenyl group. The saturated or unsaturated heterocyclic group is more preferably a 5- to 7-membered heterocyclic group having 1 to 4 nitrogen atom(s) and/or oxygen atom(s), with pyrrolidinyl, morpholino, dioxolanyl, tetrahydropyranyl, pyridyl, and tetrazolyl groups being particularly preferred. The saturated or unsaturated heterocyclic group may further have a substituent. Such a substituent is preferably a $C_{1-6}$ alkyl group (particularly methyl group) or an oxo group. The $C_{1-6}$ alkylaminocarbonyl group is more preferably ethylaminocarbonyl, dimethylamino, or methylbutylamino group. The $C_{1-6}$ alkylaminocarbonyl group may further have a substituent. Such a substituent is preferably a hydroxyl group or a $C_{1-6}$ alkoxy group (particularly methoxy group). The saturated or unsaturated heterocyclic-carbonyl group is more preferably a 5- to 7-membered saturated heterocyclic-carbonyl group having 1 or 2 nitrogen atom(s) and/or oxygen atom(s), with pyrrolidinylcarbonyl and morpholinocarbonyl groups being particularly preferred. The saturated or unsaturated heterocyclic-carbonyl group may further have a substituent. Such a substituent is preferably a halogen atom (particularly fluorine atom), or a $C_{1-6}$ alkyl group (particularly methyl group) which may have a hydroxyl group.

The $C_{6-14}$ aromatic hydrocarbon group represented as $R^2$ is more preferably a phenyl group. Specific embodiment of the substituent of the $C_{6-14}$ aromatic hydrocarbon group represented as $R^2$ is preferably a $C_{1-6}$ alkyl group, with methyl group being more preferred.

The saturated or unsaturated heterocyclic group represented as $R^2$ is a 5- to 7-membered saturated heterocycle having 1 or 2 nitrogen atom(s) or sulfur atom(s), with piperidinyl, homopiperidinyl, and tetrahydrothienyl groups being more preferred. Specific embodiment of the substituent of the saturated or unsaturated heterocyclic group represented as $R^2$ is preferably a hydroxyl group, a $C_{1-6}$ alkanoyl group, a $C_{1-6}$ alkoxycarbonyl group, a $C_{1-6}$ alkylaminocarbonyl group, or an oxo group, with a hydroxyl group, an acetyl group, an ethylaminocarbonyl group, a tert-butyloxycarbonyl group, and an oxo group being more preferred.

$R^2$ is particularly preferably methyl, methoxyethyl, morpholinoethyl, morpholinocarbonylmethyl, 2-hydroxy-n-butyl, 2-hydroxy-2-methyl-n-propyl, or 1-hydroxy-n-butan-2-yl group. In the case of 1-hydroxy-n-butan-2-yl group, an (S)-form is particularly preferred.

$R^4$ is preferably a halogen atom, with a fluorine atom and a chlorine atom being particularly preferred. The locant of $R^4$ is preferably 2-position or 3-position, with 2-position being particularly preferred.

Each of $R^5$ and $R^6$ is preferably a hydrogen atom, a halogen atom, an optionally substituted $C_{1-6}$ alkyl group, or a $C_{1-3}$ alkoxy group. The substituent of the $C_{1-6}$ alkyl group represented as $R^5$ or $R^6$ is preferably a halogen atom, with a fluorine atom being more preferred.

In one preferred case, one of $R^5$ and $R^6$ is a hydrogen atom, and the other is a hydrogen atom, a halogen atom, a trifluoromethyl group, or a methoxy group. In one more preferred embodiment, one of $R^5$ and $R^6$ is a hydrogen atom, and the other is a hydrogen atom or a halogen atom. When one of $R^5$ and $R^6$ is a hydrogen atom, and the other is a halogen atom, the locant of $R^6$ is preferably 2-position or 4-position.

In the present invention, the following acylthiourea compounds and salts thereof are particularly preferred.

4-(2-fluoro-4-(3-(2-phenylacetyl)thioureido)phenoxy)-7-methoxy-N-methylquinoline-6-carboxamide 4-(2-fluoro-4-(3-(2-phenylacetyl)thioureido)phenoxy)-7-methoxy-N-(methoxyethyl)quinoline-6-carboxamide 4-(2-fluoro-4-(3-(2-phenylacetyl)thioureido)phenoxy)-7-methoxy-N-(2-morpholinoethyl)quinoline-6-carboxamide 4-(2-fluoro-4-(3-(2-phenylacetyl)thioureido)phenoxy)-7-methoxy-N-(2-morpholino-2-oxoethyl)quinoline-6-carboxamide 4-(2-fluoro-4-(3-(2-(4-fluorophenyl)acetyl)thioureido)phenoxy)-N-(2-hydroxybutyl)-7-methoxyquinoline-6-carboxamide 4-(2-fluoro-4-(3-(2-phenylacetyl)thioureido)phenoxy)-N-(2-hydroxy-2-methylpropyl)-7-methoxyquinoline-6-carboxamide (S)-4-(2-fluoro-4-(3-(2-phenylacetyl)thioureido)phenoxy)-N-(1-hydroxybutan-2-yl)-7-methoxyquinoline-6-carboxamide 4-(2-fluoro-4-(3-(2-(4-fluorophenyl)acetyl)thioureido)phenoxy)-7-methoxy-N-(2-morpholinoethyl)quinoline-6-carboxamide (S)-4-(2-fluoro-4-(3-(2-(4-fluorophenyl)acetyl)thioureido)phenoxy)-N-(1-hydroxybutan-2-yl)-7-methoxyquinoline-6-carboxamide (S)-4-(2-fluoro-4-(3-(2-(2-fluorophenyl)acetyl)thioureido)phenoxy)-N-(1-hydroxybutan-2-yl)-7-methoxyquinoline-6-carboxamide (S)-4-(4-(3-(2-(4-chlorophenyl)acetyl)thioureido)-2-fluorophenoxy)-N-(1-hydroxybutan-2-yl)-7-methoxyquinoline-6-carboxamide The acylthiourea compound of the present invention represented as formula (I) also encompasses a steroisomer thereof, an optical isomer thereof, and a solvate thereof such as a hydrate.

The acylthiourea compound of the present invention represented as formula (I) may be a salt. The salt is preferably a pharmaceutically acceptable salt. Examples of the salt include salts of inorganic base, salts of organic base, salts with inorganic acid, salts with organic acid, salts with acidic amino acid, and salts with basic amino acid.

Specific examples of salts of inorgaic base include alkali metal (e.g., sodium or potassium) salts and alkaline earth metal (e.g., magnesium or calcium) salts.

Examples of the organic base forming the salts include trimethylamine, triethylamine, pyridine, N-methylpyridine, N-methylpyrrolidone, ethanolamine, diethanolamine, triethanolamine, and dicyclohexylamine.

Examples of the inorganic acid include hydrochloric acid, sulfuric acid, hydrobromic acid, hydroiodic acid, nitric acid, and phosphoric acid.

Examples of the organic acid include formic acid, acetic acid, propionic acid, malonic acid, succinic acid, glutaric acid, fumaric acid, maleic acid, lactic acid, malic acid, citric acid, tartaric acid, benzenesulfonic acid, p-toluenesulfonic acid, and methanesulfonic acid.

Examples of the acidic amino acid include glutamic acid and aspartic acid, and examples of the basic amino acid include lysine, asparagine, and ornithine.

The acylthiourea compound of the present invention represented as formula (I) may be a pharmaceutically acceptable produrg. No particular limitation is imposed on the pharmaceutically acceptable produrg, and any prodrug may be employed so long as the produrg can be transformed to a compound represented as formula (I) under in vivo physiological conditions (gastric acid or enzyme) via hydrolysis, oxidation, or reduction. Examples of the prodrug include ester compounds such as methyl ester, ethyl ester, propyl ester, phenyl ester, carboxyoxymethyl ester, and ethoxycarbonyl ester, which modify a carboxyl group. Examples of typical prodrugs are compounds which are transformed into compounds (I) under physiological conditions which are described in "Development of Drugs, vol. 7, p. 163-198)" published by Hirokawa Shoten (1990).

The acylthiourea compound of the present invention represented as formula (I) or a salt thereof also encompasses a hydrate thereof, a solvate thereof, and a crystal polymorph thereof.

The compound of the present invention can be produced through the below-described scheme. The raw materials required for synthesizing the compound of the present invention may be commercial products or may be produced through a method described in the literature. In the scheme, the substituents are used as the same meaning as defined in formula (I).

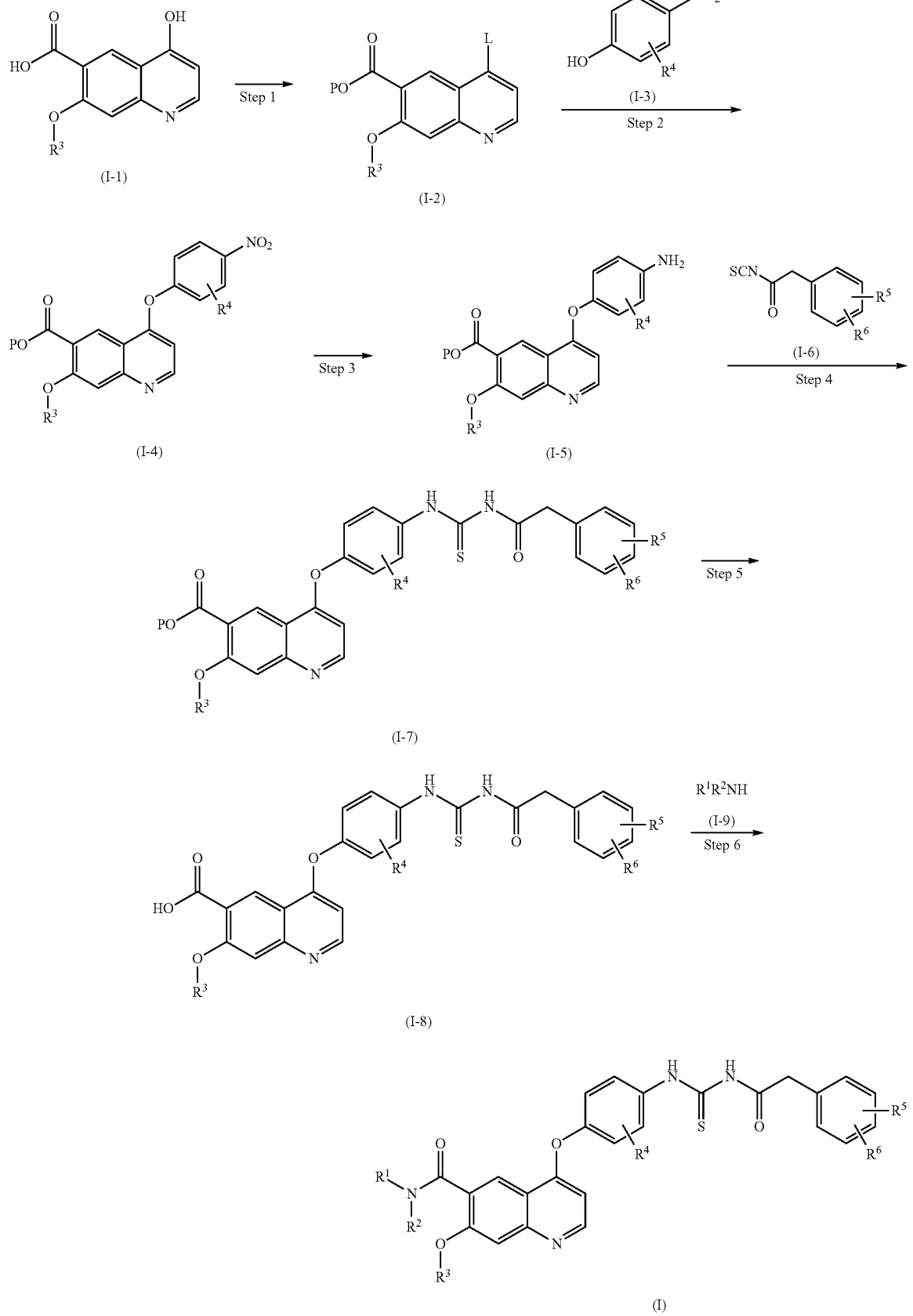

In the scheme, L represents a leaving group, P represents a lower alkyl group or a benzyl group having a substituent, specifically methyl, ethyl, methoxymethyl, tert-butyl, benzyl, 4-nitrobenzyl, 4-methoxybenzyl group, etc. Other groups are the same as defined in formula (I).

Step 1

In step 1, compound (I-2) is produced from compound (I-1). Specifically, compound (I-1), which can be produced according to the procedure disclosed in WO 2002-032872, is treated in thionyl chloride, phosphorus oxychloride, etc. serving as a solvent, to thereby introduce a halide as a leaving group L. The reaction temperature is 0° C. to reflux temperature, preferably 80° C. to reflux temperature. The reaction time is 0.1 to 100 hours, preferably 1 to 24 hours. If required, 0.001 to 1 volume, preferably 0.002 to 0.1, with respect to compound (I-1), of N,N-dimethylformamide may be added.

After completion of the above reaction, in addition to the leaving group L, the 6-position carboxyl group is also converted to acid halide. Thus, the acid halide is reacted with alcohol P—OH optionally in the presence of a base, to thereby introduce a protective group P, whereby compound (I-2) can be produced. No particular limitation is imposed on the solvent, so long as the solvent is not reactive with acid halide, and a base may be employed as the solvent. Examples of the alcohol P—OH include methanol, ethanol, tert-butanol, benzyl alcohol, 4-nitrobenzyl alcohol, and 4-methoxybenzyl alcohol. The alcohol may be used in an amount of 1 equivalent to a solvent-equivalent amount, preferably 10 equivalents to a solvent-equivalent amount. Examples of the base include organic amines such as trimethylamine, triethylamine, tripropylamine, diisopropylethylamine, N-methylmorpholine, pyridine, 4-(N,N-dimethylamino)pyridine, lutidine, and collidine; sodium hydrogencarbonate, sodium carbonate, sodium methoxide, potassium methoxide, sodium ethoxide, potassium ethoxide, and potassium tert-butoxide. The base may be used in a relative amount of 1 to 200, preferably 1.5 to 100, with respect to compound (I-1). The reaction temperature is −30° C. to reflux temperature, preferably 0 to 50° C. The reaction time is 0.1 to 100 hours, preferably 1 to 24 hours.

Step 2

Step 2 involves a coupling reaction between compound (I-2) and compound (I-3), to thereby produce compound (I-4). Compound (I-3) may be used in a relative amount of 1 to 100 equivalents, preferably 1.1 to 10 equivalents, with respect to compound (I-2). The coupling reaction is preferably performed in the presence of a base. Examples of the base include organic amines such as trimethylamine, triethylamine, tripropylamine, diisopropylethylamine, N-methylmorpholine, pyridine, 4-(N,N-dimethylamino)pyridine, lutidine, and collidine; and inorganic bases such as sodium hydrogencarbonate, sodium carbonate, potassium carbonate, and cesium carbonate. The base may be used in a relative amount of 1 to 100 equivalents, preferably 2 to 10 equivalents. No particular limitation is imposed on the solvent employed in the reaction, so long as the solvent does not readily react with compounds (I-2), (I-3), and (I-4), etc. Examples of the solvent include N,N-dimethylacetamide, diphenyl ether, chlorobenzene, 1,2-dichlorobenzene, N-methylpyrrolidin-2-one, and dimethyl sulfoxide. These solvents may be used alone or in combination. The reaction temperature is −30 to 300° C., preferably 30 to 200° C. The reaction time is 0.1 to 100 hours, preferably 0.5 to 24 hours.

Step 3

In step 3, the nitro group of compound (I-4) is reduced to thereby produce compound (I-5). Reduction of the nitro group may be performed with a reducing agent such as iron-ammonium chloride or iron-acetic acid. If compound (I-4) does not include Cl, Br, or I, or a functional group such as benzyl, 4-nitrobenzyl, or 4-methoxybenzyl, as group P, catalytic hydrogenation can be selected. When iron-ammonium chloride is used, water, methanol, ethanol, 2-propanol, tetrahydrofuran, 1,4-dioxane, toluene, methylene chloride, chloroform, acetonitrile, N,N-dimethylformamide, N,N-dimethylacetamide, N-methylpyrrolidin-2-one, dimethyl sulfoxide, etc. may be used as a solvent. These solvents may be used alone or in combination. The reaction temperature is 0 to 200° C., preferably 30 to 100° C. The reaction time is 0.1 to 100 hours, preferably 0.5 to 24 hours.

When catalytic hydrogenation is employed, examples of the catalyst employed in the reaction include 5-10% Pd—C and palladium hydroxide. The catalyst may be used in a relative amount of 0.01 to 10, preferably 0.02 to 5, with respect to compound (I-4). The hydrogen source, for example, formic acid, ammonium formate, cyclohexene, or dicyclohexene, may be used in an amount of 1 to 200 equivalents, preferably 1.1 to 100 equivalents. When hydrogen is employed, the hydrogen pressure may be 0.01 to 3.0 MPa and is preferably 0.1 to 1.0 MPa. Examples of the solvent include methanol, ethanol, tetrahydrofuran, ethyl acetate, N,N-dimethylformamide, and dimethylformamide, and these solvents may be used alone or in combination.

Step 4

In step 4, compound (I-7) is produced from compound (I-5) by use of a thioisocyanate (I-6). The thioisocyanate (I-6) may be separately produced through the procedure disclosed in WO 2005-082855 from an acid halide or a carboxylic acid. The compound (I-6) may be used in an amount of 1 to 100 equivalents with respect to compound (I-5), preferably 1.1 to 30 equivalents. No particular limitation is imposed on the solvent employed in the reaction, and hexane, toluene, tetrahydrofuran, acetonitrile, N,N-dimethylformamide, N-methylpyrrolidin-2-one, methanol, ethanol, isopropanol, etc. may be used. These solvents may be used alone or in combination. The reaction temperature is −30 to 200° C., preferably 0 to 100° C. The reaction time is 0.1 to 100 hours, preferably 0.5 to 24 hours.

Step 5

In step 5, a carboxylic acid (I-8) is produced from the ester (I-7). The reaction may be performed under basic or acidic conditions, or may be catalytic hydrogenation, whereby the ester is converted to the carboxylic acid.

When the group P is methyl or ethyl, deprotection is preferably performed under basic conditions. Examples of the base include sodium hydrogencarbonate, sodium carbonate, potassium carbonate, cesium carbonate, sodium hydroxide, potassium hydroxide, and lithium hydroxide. The base may be used in an amount of 1 to 100 equivalents, preferably 1.1 to 30 equivalents. Examples of the solvent include water, methanol, ethanol, isopropanol, tetrahydrofuran, 1,4-dioxane, and N,N-dimethylformamide. These solvents may be used alone or in combination.

When the group P is, for example, tert-butyl, deprotection is preferably performed under acidic conditions. Examples of the acid include hydrochloric acid, acetic acid, trifluoroacetic acid, sulfuric acid, and tosylic acid. The acid may be used in 1N to a solvent-equivalent amount, preferably 2N to a solvent-equivalent amount. Examples of the solvent include water, methanol, ethanol, isopropanol, ethyl acetate, tetrahydrofuran, 1,4-dioxane, methylene chloride, and chloroform. These solvents may be used alone or in combination.

When the group P is, for example, benzyl, 4-nitrobenzyl, or 4-methoxybenzyl, deprotection is preferably performed through catalytic hydrogenation in the presence of a catalyst.

The hydrogenation catalyst may be 5-10% Pd—C or palladium hydroxide. The catalyst may be used in a relative amount of 0.01 to 10 with respect to compound (I-7), preferably 0.02 to 5. The hydrogen source, for example, hydrogen, formic acid, ammonium formate, cyclohexene, or 1,4-dicyclohexene, may be used in an amount of 1 to 200 equivalents, preferably 1.1 to 100 equivalents. Examples of the solvent include methanol, ethanol, isopropanol, tetrahydrofuran, ethyl acetate, and N,N-dimethylformamide, and these solvents may be used alone or in combination.

In any combination, the reaction temperature is −30 to 200° C., preferably 0 to 100° C., and the reaction time is 0.1 to 100 hours, preferably 0.5 to 24 hours.

Step 6

Step 6 involves a condensation reaction between the carboxylic acid (I-8) and an amine (I-9). Step 6, for producing compound (I), may be performed via an acid halide from the carboxylic acid (I-8) or by use of a generally employed condensing agent.

In the procedure via acid halide, firstly, the carboxylic acid (I-8) is converted to its acid chloride by use of thionyl chloride, phosphorus oxychloride, etc. in a solvent-equivalent amount. The reaction temperature is −30 to 200° C., preferably 0 to 100° C. The reaction time is 0.1 to 100 hours, preferably 1 to 24 hours.

Then, through introducing an amine (I-9) into the thus-formed acid halide, compound (I) can be produced. If required, a base may be used. Examples of the base include organic amines such as trimethylamine, triethylamine, tripropylamine, diisopropylethylamine, N-methylmorpholine, pyridine, 4-(N,N-dimethylamino)pyridine, lutidine, and collidine; and inorganic bases such as sodium hydrogencarbonate, sodium carbonate, potassium carbonate, cesium carbonate, sodium methoxide, potassium methoxide, sodium ethoxide, potassium ethoxide, and potassium tert-butoxide. The amine (I-9) may be used in an amount of 1 to 100 equivalents, preferably 1.1 to 50 equivalents. Examples of the solvent employed in the reaction include tetrahydrofuran, 1,4-dioxane, toluene, methylene chloride, chloroform, acetonitrile, N,N-dimethylformamide, N,N-dimethylacetamide, and dimethyl sulfoxide.

Alternatively, a condensing agent may be used in production of compound (I). Examples of the condensing agent include N,N'-dicyclohexylcarbodiimide (DCC), N,N'-diisopropylcarbodiimide (DIC), 1-ethyl-3-(3-dimethylaminopropyl)carbodiimide hydrochloride (WSC), diphenylphosphoryl azide (DPPA), benzotriazol-1-yl-oxytris(dimethylamino) phosphonium hexafluorophosphate (BOP), benzotriazol-1-yl-oxytripyrrolidinophosphonium hexafluorophosphate (PyBOP), 7-azabenzotriazol-1-yl-oxytris(pyrrolidino) phosphonium phosphate (PyAOP), bromotris(pyrrolidino) phosphonium hexafluorophosphate (BroP), chlorotris (pyrrolidin-1-yl)phosphonium hexafluorophosphate (PyCroP), 3-(diethoxyphosphoryloxy)-1,2,3-benzotriazin-4 (3H)-one (DEPBT), O-(benzotriazol-1-yl)-N,N,N',N'-tetramethyluronium hexafluorophosphate (HATU), and 4-(5,6-dimethoxy-1,3,5-triazin-2-yl)-4-methylmorpholine hydrochloride (DMTMM). In combination with the condensing agent, additives such as 1-hydroxybenzotriazole (HOBt), 1-hydroxy-7-azabenzotriazole (HOAt), and N-hydroxysuccinimide (HOSu) may be used. These additives may be used in amounts of 0.1 to 100 equivalents, preferably 1 to 10 equivalents. If required, a base such as trimethylamine, triethylamine, tripropylamine, diisopropylethylamine, N-methylmorpholine, pyridine, 4-(N,N-dimethylamino)pyridine, lutidine, or collidine may be used in an amount of 0.1 to 100 equivalents, preferably 1 to 10 equivalents. The amine (I-9) may be used in the same amount as mentioned above. No particular limitation is imposed on the solvent, and water, methanol, ethanol, 2-propanol, tetrahydrofuran, 1,4-dioxane, toluene, methylene chloride, chloroform, acetonitrile, N,N-dimethylformamide, N,N,-dimethylacetamide, dimethyl sulfoxide, etc. may be employed. The reaction temperature is −30 to 200° C., preferably 0 to 100° C. The reaction time is 0.1 to 100 hours, preferably 0.5 to 24 hours.

Other than the above-mentioned procedures, the compound (I-5) may be transformed to its amide according to steps 5 and 6, and then compound (I) may be produced according to step 4. When the group P is methyl, the compound (I-5) may be transformed to its amide through a generally known technique such as aminolysis, and then compound (I) may be produced according to step 4.

The thus-produced compound of the present invention and synthesis intermediates therefor may be isolated and purified through generally known isolation/purification means (e.g., recrystallization, crystallization, distillation, or column chromatography). Generally, the compound of the present invention and synthesis intermediates therefor can be transformed to pharmaceutically acceptable salts thereof through a known method, and the salts can be transformed to the free forms thereof.

When employed as a drug, the compound (I) of the present invention is mixed with an optional pharmaceutical carrier, and the mixture may be formed into a variety of dosage forms in accordance with the preventive or therapeutic purposes. Any dosage forms may be employed, and examples include oral agents, injection liquids, suppositories, ointments, and cataplasms. Of these, oral agents are preferably employed. These dosage forms may be produced through methods generally known and employed in the art.

As pharmaceutical carriers, a variety of organic and inorganic carrier substances which are generally employed for forming formulations may be used. Examples of the carrier for solid formulation include an excipient, a binder, a disintegrant, a lubricant, and a colorant, and examples of the carrier for liquid formulation include a solvent, a solubilizing agent, a suspending agent, a tonicity agent, a buffer, and a soothing agent. If required, formulation additives such as a preservative, an antioxidant, a colorant, a sweetening agent, and a stabilizer may also be used.

A peroral solid form may be prepared through mixing the compound of the present invention with an excipient, and with an optional excipient, binder, disintegrant, lubricant, colorant, flavoring/deodorizing agent, etc., and forming the mixture into tablets, coated-tablets, granules, powder, capsules, etc. through a method known in the art.

Examples of the excipient include lactose, sucrose, D-mannitol, glucose, starch, calcium carbonate, kaolin, microcrystalline cellulose, and anhydrous silicic acid.

Examples of the binder include water, ethanol, 1-propanol, 2-propanol, simple syrup, liquid glucose, liquid α-starch, liquid gelatin, D-mannitol, carboxymethyl cellulose, hydroxypropyl cellulose, hydroxypropyl starch, methyl cellulose, ethyl cellulose, shellac, calcium phosphate, and polyvinylpyrrolidone.

Examples of the disintegrant include dry starch, sodium alginate, powdered agar, sodium hydrogencarbonate, calcium carbonate, sodium lauryl sulfate, monoglyceryl stearate, and lactose.

Examples of the lubricant include purified talc, sodium stearate (salt), magnesium stearate, borax, and polyethylene glycol.

Examples of the colorant include titanium oxide and iron oxide.

Examples of the flavoring/deodorizing agent include sucrose, orange peel, citric acid, and tartaric acid.

An oral liquid formulation may be prepared by mixing the compound of the present invention with a flavoring agent, buffer, stabilizer, deodorant, etc., and forming the mixture into internal liquid agent, syrup, elixir, etc. through a method known in the art. The flavoring/deodorizing agent employed in the preparation may be any of the aforementioned members. Examples of the buffer include sodium citrate. Examples of the stabilizer include traganth, gum arabic, and gelatin. If required, the oral formulation may be coated through a known method with an enteric coating material or a coating material for maintaining the effect thereof. Examples of such a coating material include hydroxypropylmethyl cellulose, ethyl cellulose, hydroxymethyl cellulose, hydroxypropyl cellulose, polyoxyethylene glycol, and Tween 80 (registered trademark).

Injection solutions may be prepared by mixing the compound of the present invention with additives such as a pH-regulator, buffer, stabilizer, tonicity agent, and local anesthetic agent, and forming the mixture through a method known in the art, to thereby provide subcutaneous, intramuscular, and intravenous injection liquids. Examples of the pH-regulator and buffer include sodium citrate, sodium acetate, and sodium phosphate. Examples of the stabilizer include sodium pyrosulfite, EDTA, thioglycolic acid, and thiolactic acid. Examples of the local anesthetic include procaine hydrochloride and lidocaine hydrochloride. Examples of the tonicity agent include sodium chloride, glucose, D-mannitol, and glycerin.

Suppositories may be prepared by mixing the compound of the present invention with a carrier for formulation known in the art such as polyethylene glycol, lanolin, cacao butter, and fatty acid triglyceride, and with an optional surfactant such as Tween 80 (registered trademark), and forming the mixture into suppositories through a method known in the art.

Ointments may be prepared by mixing the compound of the present invention with optional additives generally employed in the art such as a base, stabilizer, moisturizer, and preservative, and forming the mixture into ointments through a method known in the art. Examples of the base include liquid paraffin, white petrolatum, white beeswax, octyldodecyl alcohol, and paraffin. Examples of the preservative include methyl p-hydroxybenzoate, ethyl p-hydroxybenzoate, and propyl p-hydroxybenzoate.

Cataplasms may be prepared by applying the aforementioned ointment, cream, gel, paste, etc. to a generally employed support through a routine method. Examples of appropriate supports include woven and nonwoven fabric made of cotton, staple fiber, or chemical fiber, and film and foamed sheet made of soft vinyl chloride, polyethylene, polyurethane, etc.

The amount of the compound of the present invention incorporated into any of the aforementioned unit dosage forms is varied in accordance with the form of the drug and the symptom of the patient to which the compound is administered. However, generally, in a unit dosage form, the amount is preferably about 0.05 to 1,000 mg (oral agent), about 0.01 to 500 mg (injection solution), or about 1 to 1,000 mg (suppository).

The daily dose of the drug having any of the above dosage forms varies in accordance with the symptom, body weight, age, sex, etc. of a patient and cannot be determined unequivocally. However, the daily dose for an adult (body weight: 50 kg) is generally about 0.05 to 5,000 mg, preferably 0.1 to 1,000 mg. Preferably, the drug is administered at a single daily dose or in a divided (e.g., 2 or 3) manner.

EXAMPLES

Detailed embodiments of the present invention is described by way of Examples and Pharmacological Test Examples, which should not be construed as limiting the invention thereto.

Example 1 tert-Butyl 4-chloro-7-methoxyquinoline-6-carboxylate (1a)

4-Hydroxy-7-methoxyquinoline-6-carboxylic acid, (disclosed in WO 2002/032872) (25 g) was dissolved in thionyl chloride (100 mL), and N,N-dimethylformamide (5 mL) was added to the solution, followed by refluxing under heating for 2 hours. The reaction mixture was concentrated under reduced pressure and azeotroped with toluene. The product was added to a solution of tert-butoxypotassium (150 g, 6-fold amount) in tert-butanol (300 mL) on an ice bath, followed by stirring for 17 hours. The reaction mixture was concentrated under reduced pressure, and water (300 mL) was added thereto on an ice bath, followed by extraction with n-hexane (300 mL). The organic phase was washed with saturated brine (300 mL) and dried over sodium sulfate, followed by concentration under reduced pressure, to thereby yield compound 1a (10.5 g, yield: 31%).

$^1$H-NMR (CDCl$_3$) δ: 8.73 (1H, d, J=4.2 Hz), 8.50 (1H, s), 7.49 (1H, s), 7.38 (1H, d, J=4.8 Hz), 4.03 (3H, s), 1.64 (9H, s); ESI-MS m/z 294 (MH$^+$).

tert-Butyl 4-(2-fluoro-4-nitrophenoxy)-7-methoxyquinoline-6-carboxylate (1b)

Compound 1a (3.60 g) was dissolved in N-methylpyrrolidin-2-one (14 mL), and diisopropylethylamine (6.55 mL) and 2-fluoro-4-nitrophenol (2.89 g) were added to the solution. The mixture was heated to 140° C. and stirred for 4 hours. To the reaction mixture, distilled water was added on an ice bath, and the precipitate was filtrated, to thereby yield compound 1b (4.71 g, yield: 93%).

$^1$H-NMR (DMSO-d$_6$) δ: 8.75 (1H, d, J=4.8 Hz), 8.47 (1H, dd, J=10.4 Hz, 2.8 Hz), 8.38 (1H, s), 8.23 (1H, ddd, J=8.8 Hz, 1.2 Hz, 1.2 Hz), 7.74 (1H, t, J=8.0 Hz), 7.55 (1H, s), 6.78 (1H, d, J=5.2 Hz), 3.99 (3H, s), 1.54 (9H, s); ESI-MS m/z 415 (MH$^+$).

tert-Butyl 4-(4-amino-2-fluorophenoxy)-7-methoxyquinoline-6-carboxylate (1c)

Compound 1b (400 mg) was dissolved in a water-ethanol (1:1) mixture (10 mL), and iron powder (1.0 g) and ammonium chloride (1.0 g) were added thereto, followed by stirring at 80° C. for 2 hours. The reaction mixture was filtered through Celite to thereby remove iron powder, and water (100 mL) was added to the filtrate, followed by extraction with ethyl acetate (50 mL). The organic phase was washed with saturated brine (100 mL) and dried over sodium sulfate, followed by concentration under reduced pressure, to thereby yield compound 1c (335 mg, yield: 93%).

$^1$H-NMR (DMSO-d$_6$) δ: 8.65 (1H, d, J=5.2 Hz), 8.40 (1H, s), 7.48 (1H, s), 7.10 (1H, t, J=9.2 Hz), 6.55 (1H, dd, J=13.2 Hz, 2.8 Hz), 6.48-6.44 (2H, m), 5.51 (2H, s), 3.96 (3H, s), 1.55 (9H, s); ESI-MS m/z 385 (MH$^+$).

tert-Butyl 4-(2-fluoro-4-(3-(2-phenylacetyl)thioureido)phenoxy)-7-methoxyquinoline-6-carboxylate (1d)

Phenylacetyl chloride (1.10 mL) and potassium thiocyanate (1.21 g) were dissolved in acetonitrile (15 mL), followed by stirring at 70° C. for 2 hours. The reaction mixture was cooled to room temperature and concentrated under reduced pressure. Subsequently, the product was separated with aqueous saturated solution of sodium hydrogencarbonate (100 mL) and ethyl acetate (50 mL). The organic layer was washed with saturated brine (100 mL) and dried over sodium sulfate, followed by concentration under reduced pressure, to thereby yield phenylacetyl thioisocyanate. This product (phenylacetyl thioisocyanate) was not subjected to further purification and dissolved in toluene (8 mL). A solution (12 mL) of compound 1c in toluene-ethanol (5:1) was added to the toluene solution, followed by stirring at room temperature for 3 hours. The reaction mixture was concentrated under reduced pressure and purified through silica gel column chromatography (eluent: 100% ethyl acetate), to thereby yield compound 1d (620 mg, yield: 53%).

$^1$H-NMR (CDCl$_3$) δ: 12.62 (1H, s), 8.70 (1H, s), 8.58 (1H, s), 8.09 (1H, dd, J=11.8 Hz, 2.0 Hz), 7.81 (1H, s), 7.51-7.30 (7H, m), 6.71 (1H, s), 4.18 (3H, s), 3.78 (2H, s), 1.64 (6H, s); ESI-MS m/z 562 (MH$^+$).

4-(2-Fluoro-4-(3-(2-phenylacetyl)thioureido)phenoxy)-7-methoxyquinoline-6-carboxylic acid hydrochloride (1e)

Compound 1d (88.0 mg) was dissolved in 4N HCl-dioxane solution, followed by stirring at 70° C. for 1 hour. The precipitate in the reaction mixture was filtrated, to thereby yield compound 1e (67.1 mg, yield: 79%).

$^1$H-NMR (DMSO-d$_6$) δ: 12.54 (1H, s), 11.86 (1H, s), 8.98 (1H, d, J=6.4 Hz) 8.70 (1H, s), 8.11 (1H, d, J=12.4 Hz), 7.74.-7.73 (1H, m), 7.65-7.60 (2H, m), 7.37-7.32 (4H, m), 7.30-7.25 (1H, m), 6.91 (1H, d, J=6.0 Hz), 4.04 (3H, s), 3.83 (2H, s); ESI-MS m/z 506 (MH$^+$).

4-(2-Fluoro-4-(3-(2-phenylacetyl)thioureido)phenoxy)-N-(3-isopropyloxypropyl)-7-methoxyquinoline-6-carboxamide (1)

Compound 1e (13.2 mg), 3-isopropoxypropylamine (9.11 μL), and 4-(5,6-dimethoxy-1,3,5-triazin-2-yl)-4-methylmorpholine hydrochloride n-hydrate (hereinafter referred to as DMTMM•n-hydrate) (8.67 mg) were dissolved in tetrahydrofuran (1 mL), followed by stirring at room temperature for 2 hours. The reaction mixture was distilled under reduced pressure, and water was added to the residue. The precipitate was filtrated, to thereby yield the titled compound 1 (11.6 mg, yield: 79%).

$^1$H-NMR (DMSO-d$_6$) δ: 12.51 (1H, s), 11.83 (1H, s), 8.69 (1H, d, J=5.6 Hz) 8.54 (1H, s), 8.39 (1H, t, J=4.8 Hz), 8.04 (1H, dd, J=12.4 Hz, J=2.0 Hz), 7.58-7.49 (3H, m), 7.39-7.34 (4H, m), 7.32-7.27 (1H, m), 6.53 (1H, d, J=5.2 Hz), 4.02 (3H, s), 3.84 (2H, s), 3.58-3.50 (1H, m), 3.45 (2H, t, J=6.0 Hz), 3.40-3.36 (2H, m), 1.79-1.68 (2H, m), 1.09 (6H, d, J=6.0 Hz); ESI-MS m/z 605 (MH$^+$).

Example 2

N-((2,2-Dimethyl-1,3-dioxolan-4-yl)methyl)-4-(2-fluoro-4-(3-(2-phenylacetyl)thioureido)phenoxy)-7-methoxyquinoline-6-carboxamide (2)

Similar to the synthesis of Example 1, from compound 1e (19.4 mg), (2,2-dimethyl-1,3-dioxolan-4-yl)methaneamine (13.5 μL), and DMTMM•n-hydrate (11.9 mg), the titled compound 2 was yielded (9.3 mg, yield: 42%).

$^1$H-NMR (CDCl$_3$) δ: 12.50 (1H, s), 9.26 (1H, s), 8.66 (1H, dd, J=5.4 Hz, 0.8 Hz), 8.52 (1H, s), 8.23 (1H, t, J=5.6 Hz), 7.96 (1H, dd, J=11.2 Hz, J=2.8 Hz), 7.53 (1H, s), 7.46-7.37 (4H, m), 7.32-7.28 (3H, m), 6.44 (1H, dd, J=7.2 Hz), 4.43-4.38 (1H, m), 4.13-4.09 (1H, m), 4.12 (3H, s), 3.79-3.71 (3H, m), 2.42 (2H, t, J=8.0 Hz), 3.76 (2H, s), 1.49 (3H, s), 1.43 (1H, s), 1.39 (2H, s); ESI-MS m/z 619 (MH$^+$).

Example 3

N-(2,3-Dihydroxypropyl)-4-(2-fluoro-4-(3-(2-phenylacetyl)thioureido)phenoxy)-7-methoxyquinoline-6-carboxamide (3)

Similar to the synthesis of Example 1, from compound 1e (20.1 mg), 3-amino-1,2-propanediol (8.45 mg), and DMTMM•n-hydrate (12.3 mg), the titled compound 3 was yielded (5.1 mg, yield: 24%).

$^1$H-NMR (DMSO-d$_6$) δ: 12.50 (1H, s), 11.82 (1H, s), 8.69 (1H, s), 8.69 (1H, d, J=5.2 Hz), 8.48 (1H, t, J=5.6 Hz), 8.39 (1H, t, J=4.8 Hz), 8.04 (1H, dd, J=12.0 Hz, J=2.4 Hz), 7.58-7.50 (3H, m), 7.37-7.33 (4H, m), 7.31-7.26 (1H, m), 6.52 (1H, d, J=5.4 Hz), 4.92 (1H, br), 4.65 (1H, br), 4.03 (3H, s), 3.82 (2H, s), 3.65 (1H, t, J=5.6 Hz), 3.52-3.46 (1H, m), 3.43-3.37 (3H, m, J=6.0 Hz); ESI-MS m/z 579 (MH$^+$).

Example 4

4-(2-Fluoro-4-(3-(2-phenylacetyl)thioureido)phenoxy)-7-methoxy-N-(pyridin-3-ylmethyl)quinoline-6-carboxamide (4)

Similar to the synthesis of Example 1, from compound 1e (16.7 mg), 3-picolylamine (7.79 μL), and DMTMM•n-hydrate (10.2 mg), the titled compound 4 was yielded (8.1 mg, yield: 44%).

$^1$H-NMR (DMSO-d$_6$) δ: 12.50 (1H, s), 11.81 (1H, s), 9.01 (1H, t, J=7.6 Hz), 8.69 (1H, d, J=5.2 Hz), 8.58 (1H, d, J=1.6 Hz), 8.57 (1H, s), 8.45 (1H, dd, J=4.8 Hz, 1.0 Hz), 8.02 (1H, dd, J=12.8 Hz, 1.6 Hz), 7.77 (1H, d, J=8.0 Hz), 7.56-7.48 (4H, m), 7.39-7.33 (6H, m), 7.31-7.26 (1H, m), 6.52 (1H, d, J=5.6 Hz), 4.55 (2H, d, J=6.0 Hz), 4.03 (3H, s), 3.82 (2H, s); ESI-MS m/z 596 (MH$^+$).

Example 5

4-(2-Fluoro-4-(3-(2-phenylacetyl)thioureido)phenoxy)-7-methoxy-N-(3-(2-oxopyrrolidin-1-yl)propyl)quinoline-6-carboxamide (5)

Similar to the synthesis of Example 1, from compound 1e (18.8 mg), N-(3'-aminopropyl)-2-pyrrolidinone (12.2 μL), and DMTMM•n-hydrate (11.5 mg), the titled compound 5 was yielded (5.5 mg, yield: 25%).

$^1$H-NMR (CDCl$_3$) δ: 12.53 (1H, s), 9.24 (1H, s), 8.76 (1H, s), 8.65 (1H, d, J=5.6 Hz), 8.53 (1H, t, J=6.0 Hz), 7.95 (1H, dd, J=12.0 Hz, J=2.4 Hz), 7.52 (1H, s), 7.45-7.37 (4H, m), 7.32-7.30 (2H, m), 7.23 (1H, d, J=8.4 Hz), 6.42 (1H, dd, J=5.2 Hz, 1.2 Hz), 4.17 (3H, s), 3.76 (2H, s), 3.52-3.42 (6H, m), 2.42 (2H, t, J=8.0 Hz), 2.06 (2H, tt, J=7.6 Hz), 1.86 (2H, tt, J=6.0 Hz); ESI-LRMS m/z 630 (MH$^+$).

Example 6

4-(2-Fluoro-4-(3-(2-phenylacetyl)thioureido)phenoxy)-7-methoxy-N-methylquinoline-6-carboxamide (6)

Similar to the synthesis of Example 1, compound 1e (20 mg), 40% aqueous solution of methylamine (5 μL), and DMTMM•n-hydrate (22 mg) were dissolved in tetrahydrofuran (1 mL), followed by stirring at 30° C. for 1 hour, to thereby yield the titled compound 6 (18.4 mg, yield: 96%).

$^1$H-NMR (DMSO-$d_6$) δ: 12.51 (1H, s), 11.83 (1H, s), 8.69 (1H, d, J=4.8 Hz), 8.60 (1H, s), 8.38 (1H, d, J=4.8 Hz), 8.03 (1H, dd, J=12.4 Hz, J=2.0 Hz), 7.58-7.50 (4H, m), 7.39-7.34 (4H, m), 6.53 (1H, d, J=5.2 Hz), 4.03 (3H, s), 3.84 (2H, s), 2.84 (3H, d, J=4.8 Hz); ESI-MS m/z 518 (MH$^+$).

Example 7

4-(2-Fluoro-4-(3-(2-phenylacetyl)thioureido)phenoxy)-7-methoxy-N-(methoxyethyl)quinoline-6-carboxamide (7)

Similar to the synthesis of Example 1, compound 1e (20 mg), 2-methoxyethyleneamine (6 mg), DMTMM•n-hydrate (22 mg) were dissolved in ethanol (1 mL), followed by stirring at 30° C. for 1 hour, to thereby yield the titled compound 7 (17.3 mg, yield: 83%).

$^1$H-NMR (DMSO-$d_6$) δ: 12.51 (1H, s), 11.83 (1H, s), 8.71-8.69 (1H, m), 8.62 (1H, s), 8.54-8.44 (1H, m), 8.04 (1H, dd, J=12.4 Hz, 1.6 Hz), 7.58-7.50 (3H, m), 7.36-7.34 (4H, m), 7.32-7.27 (1H, m), 6.53 (1H, d, J=4.8 Hz), 4.04 (3H, s), 3.84 (2H, s), 3.50-3.48 (4H, m), 3.30 (3H, s); ESI-MS m/z 562 (MH$^+$).

Example 8

N-(2-(Diethylamino)ethyl)-4-(2-fluoro-4-(3-(2-phenylacetyl)thioureido)phenoxy)-7-methoxyquinoline-6-carboxamide (8)

Similar to the synthesis of Example 1, from compound 1e (22.6 mg), 2-(diethylamino)ethylamine (14.8 μL), and DMTMM•n-hydrate (13.8 mg), the titled compound 8 was yielded (12.3 mg, yield: 49%).

$^1$H-NMR (DMSO-$d_6$) δ: 12.50 (1H, s), 11.83 (1H, s), 8.73-8.70 (1H, m), 8.72 (1H, s), 8.51 (1H, t, J=5.2 Hz), 8.04 (1H, dd, J=12.8 Hz, 1.6 Hz), 7.58-7.50 (3H, m), 7.38-7.33 (4H, m), 7.31-7.27 (1H, m), 6.53 (1H, d, J=6.0 Hz), 4.05 (3H, s), 3.84 (2H, s), 3.42-3.37 (2H, m), 2.67-2.53 (6H, m), 1.01 (6H, t, J=7.2 Hz); ESI-MS m/z 604 (MH$^+$).

Example 9

4-(2-Fluoro-4-(3-(2-phenylacetyl)thioureido)phenoxy)-7-methoxy-N-(2-morpholinoethyl)quinoline-6-carboxamide (9)

Similar to the synthesis of Example 1, from compound 1e (9.6 mg), 2-morpholinoethylamine (5.77 μL), and DMTMM•n-hydrate (5.88 mg), the titled compound 9 was yielded (3.3 mg, yield: 30%).

$^1$H-NMR (CDCl$_3$) δ: 12.53 (1H, s), 9.26 (1H, s), 9.08 (1H, t, J=3.6 Hz), 8.72 (1H, s), 8.66 (1H, d, J=5.0 Hz), 7.95 (1H, dd, J=11.6 Hz, 2.4 Hz), 7.55 (1H, s), 7.45-7.36 (4H, m), 7.32-7.24 (3H, m), 6.44 (1H, dd, J=5.2 Hz, 0.8 Hz), 4.37 (2H, d, J=4.0 Hz), 4.18 (3 H, s), 3.79-3.72 (7H, m), 3.77 (2H, s), 3.52 (2H, t, J=4.8 Hz); ESI-MS m/z 618 (MH$^+$).

Example 10

4-(2-Fluoro-4-(3-(2-phenylacetyl)thioureido)phenoxy)-N-(2-(2-hydroxyethoxy)ethyl)-7-methoxyquinoline-6-carboxamide (10)

Similar to the synthesis of Example 1, from compound 1e (9.7 mg), 2-(2-aminoethoxy)ethanol (4.44 μL), and DMTMM•n-hydrate (5.94 mg), the titled compound 10 was yielded (3.0 mg, yield: 28%).

1H-NMR (DMSO-$d_6$) δ: 12.51 (1H, s), 11.83 (1H, s), 8.70 (1H, d, J=5.2 Hz), 8.64 (1H, s), 8.49 (1H, t, J=5.2 Hz), 8.04 (1H, d, J=12.2 Hz), 7.58-7.50 (3H, m), 7.38-7.34 (4H, m), 7.31-7.27 (1H, m), 6.52 (1H, d, J=5.2 Hz), 4.62 (1H, t, J=5.2 Hz), 4.04 (3H, s), 3.84 (2H, s), 3.58 (2H, t, J=5.6 Hz), 3.54-3.47 (6H, m); ESI-MS m/z 592 (MH$^+$).

Example 11

N-(2-Acetamidoethyl)-4-(2-fluoro-4-(3-(2-phenylacetyl)thioureido)phenoxy)-7-methoxyquinoline-6-carboxamide (11)

Similar to the synthesis of Example 1, from compound 1e (20.7 mg), N-acetylethylenediamine (9.75 mg), and DMTMM•n-hydrate (12.7 mg), the titled compound 11 was yielded (5.4 mg, yield: 20%).

$^1$H-NMR (DMSO-$d_6$) δ: 12.49 (1H, s), 11.82 (1H, s), 8.68 (1H, dd, J=5.2 Hz, 2.8 Hz), 8.63 (1H, d, J=2.4 Hz), 8.48 (1H, t, J=5.6 Hz), 8.02 (1H, d, J=12.4 Hz), 7.98 (1H, s), 7.56-7.49 (3H, m), 7.36-7.32 (4H, m), 7.30-7.26 (1H, m), 6.51 (1H, d, J=5.2 Hz) 4.02 (3H, s), 3.82 (2H, s), 3.38-3.35 (2H, m), 3.28-3.22 (2H, s), 1.82 (3H, s); ESI-MS m/z 590 (MH$^+$).

Example 12

N-(1,3-Dihydroxypropan-2-yl)-4-(2-fluoro-4-(3-(2-phenylacetyl)thioureido)phenoxy)-7-methoxyquinoline-6-carboxamide (12)

Similar to the synthesis of Example 1, from compound 1e (37.1 mg), 2-amino-1,3-propanediol (15.6 mg), and DMTMM•n-hydrate (22.7 mg), the titled compound 12 was yielded (11.5 mg, yield: 29%).

$^1$H-NMR (DMSO-$d_6$) δ: 12.50 (1H, s), 11.82 (1H, s), 8.74 (1H, s), 8.69 (1H, d, J=5.2 Hz), 8.29 (1H, d, J=8.0 Hz), 8.03 (1H, dd, J=12.0 Hz, 2.0 Hz), 7.57-7.50 (3H, m), 7.35-7.33 (4H, m), 7.31-7.26 (1H, m), 6.52 (1H, d, J=5.2 Hz), 4.80 (2H, t, J=5.2 Hz), 4.04 (3H, s), 3.99-3.94 (1H, m), 3.83 (2H, s), 3.61-3.56 (2H, m), 3.54-3.47 (2H, m); ESI-MS m/z 579 (MH$^+$).

Example 13 tert-Butyl 4-(4-(2-fluoro-4-(3-(2-phenylacetyl)thioureido)phenoxy)-7-methoxyquinoline-6-carboxamido)-6-carboxamido)piperidine-1-carboxylate (13)

Similar to the synthesis of Example 1, from compound 1e (750 mg), 4-amino-1-Boc-piperidine (332 mg), triethylamine (230 μL), and DMTMM•n-hydrate (459 mg), the titled compound 13 was yielded (446 mg, yield: 52%).

$^1$H-NMR (CDCl$_3$) δ: 12.50 (1H, s), 9.24 (1H, s), 8.66 (1H, d, J=5.4 Hz), 8.49 (1H, s), 7.96 (1H, dd, J=11.6 Hz, 2.4 Hz), 7.83 (1H, d, J=7.6 Hz), 7.53 (1H, s), 7.47-7.37 (4H, m), 7.33-7.29 (3H, m), 6.44 (1H, d, J=5.0 Hz, 1.2 Hz), 4.23 (1H, br), 4.11 (3H, s), 4.03-4.01 (1H, m), 3.76 (2H, s), 3.04 (3H, t, J=12.0 Hz), 2.92 (1H, t, J=10.8 Hz), 2.09-1.98 (3H, m), 1.48 (9H, s); ESI-MS m/z 688 (MH$^+$).

Example 14

4-(2-Fluoro-4-(3-(2-phenylacetyl)thioureido)phenoxy)-7-methoxy-N-(piperidin-4-yl)quinoline-6-carboxamide dihydrochloride (14)

Compound 13 (446 mg) was dissolved in 4N HCl-dioxane solution, followed by stirring at room temperature for 1 hour. The reaction mixture was concentrated under reduced pressure, and the residue was azeotroped with toluene, to thereby yield the titled compound 14 (406 mg, yield: 95%).

$^1$H-NMR (DMSO-d$_6$) δ: 12.50 (1H, s), 11.82 (1H, s), 8.67 (1H, d, J=5.2 Hz), 8.44 (1H, s), 8.30 (1H, d, J=7.6 Hz), 8.02 (1H, dd, J=12.8 Hz, 1.6 Hz), 7.57-7.44 (3H, m), 7.37-7.33 (4H, m), 7.31-7.26 (1H, m), 6.51 (1H, d, J=5.2 Hz), 4.04-3.96 (1H, br), 3.99 (3H, s), 3.93 (2H, s), 3.96-3.79 (4H, m), 3.83 (2H, s), 2.92 (2H, br), 1.83 (1H, m); ESI-MS m/z 588 (MH$^+$).

Example 15

N-(1-(Ethylcarbamoyl)piperidin-4-yl)-4-(2-fluoro-4-(3-(2-phenylacetyl)thioureido)phenoxy)-7-methoxyquinoline-6-carboxamide (15)

Compound 14 (335 mg) was suspended in tetrahydrofuran (5 mL), and triethylamine (212 μL) and ethyl isocyanate (71.2 μL) were added to the suspension, followed by stirring at room temperature for 15 hours. The reaction mixture was concentrated under reduced pressure, and the formed solid was filtrated, to thereby yield titled compound 15 (271 mg, yield: 81%).

$^1$H-NMR (DMSO-d$_6$) δ: 12.50 (1H, s), 11.82 (1H, s), 8.67 (1H, d, J=5.6 Hz), 8.44 (1H, s), 8.28 (1H, d, J=8.0 Hz), 8.02 (1H, d, J=12.8), 7.56-7.48 (3H, m), 7.35-7.28 (5H, m), 6.51 (1H, d, J=4.8 Hz), 6.45 (1H, t, J=4.8 Hz), 3.99 (4H, s), 3.88 (2H, d, J=12.8 Hz), 3.82 (2H, s), 3.06-2.99 (2H, m), 2.82 (3H, t, J=12.0 Hz), 1.43-1.34 (3H, m), 0.99 (3H, t, J=7.2 Hz); ESI-MS m/z 659 (MH$^+$).

Example 16

4-(2-Fluoro-4-(3-(2-phenylacetyl)thioureido)phenoxy)-7-methoxy-N-(2-oxoazepan-3-yl)quinoline-6-carboxamide (16)

Similar to the synthesis of Example 1, from compound 1e (260 mg), DL-α-amino-ε-caprolactam (73.7 mg), triethylamine (134 μL), and DMTMM•n-hydrate (159 mg), the titled compound 16 was yielded (221 mg, yield: 75%).

$^1$H-NMR (DMSO-d$_6$) δ: 12.50 (1H, s), 11.82 (1H, s), 9.19 (1H, d, J=6.0 Hz), 8.90 (1H, s), 8.71 (1H, d, J=5.2 Hz), 8.05-7.96 (2H, m), 7.60-7.51 (3H, m), 7.37-7.33 (4H, m), 7.31-7.26 (1H, m), 6.53 (1H, d, J=4.4 Hz), 4.65-4.61 (1H, m), 4.10 (3H, s), 3.96 (2H, s), 3.83 (2H, s), 2.07 (1H, d, J=12.8 Hz), 1.94-1.90 (1H, m), 1.79-1.69 (2H, m), 1.47-1.38 (1H, m), 1.29-1.20 (1H, m); ESI-MS m/z 616 (MH$^+$).

Example 17

4-(2-Fluoro-4-(3-(2-phenylacetyl)thioureido)phenoxy)-7-methoxy-N-(2-oxo-2-(pyrrolidin-1-yl)ethyl)quinoline-6-carboxamide (17)

Similar to the synthesis of Example 1, from compound 1e (304 mg), 2-amino-1-(pyrrolidin-1-yl)ethanone hydrochloride (120 mg), triethylamine (235 μL), and DMTMM•n-hydrate (186 mg), the titled compound 17 was yielded (220 mg, yield: 64%).

$^1$H-NMR (DMSO-d$_6$) δ: 12.50 (1H, s), 11.82 (1H, s), 8.83 (2H, d, J=1.2 Hz), 8.71 (1H, dd, J=5.2 Hz, 1.6 Hz), 8.05-7.99 (1H, m), 7.60-7.53 (3H, m), 7.35-7.33 (4H, m), 7.30-7.28 (1H, m), 6.53 (1H, d, J=5.2 Hz), 4.14 (2H, d, J=4.0 Hz), 4.08 (3H, d, J=1.2 Hz), 3.83 (2H, s), 3.48-3.44 (2H, m), 3.39-3.24 (2H, m), 1.94-1.88 (2H, m), 1.83-1.76 (2H, m); ESI-MS m/z 616 (MH$^+$).

Example 18

N-(1-Acetylpiperidin-4-yl)-4-(2-fluoro-4-(3-(2-phenylacetyl)thioureido)phenoxy)-7-methoxyquinoline-6-carboxamide (18)

Similar to the synthesis of Example 1, from compound 1e (14.3 mg), 1-(4-aminopiperidin-1-yl)ethanone hydrochloride (5.66 mg), triethylamine (9.21 μL), and DMTMM•n-hydrate (8.76 mg), the titled compound 18 was yielded (6.0 mg, yield: 36%).

$^1$H-NMR (DMSO-d$_6$) δ: 12.50 (1H, s), 11.82 (1H, s), 8.67 (2H, d, J=5.2 Hz), 8.45 (1H, s), 8.02 (1H, dd, J=12.4 Hz, 2.4 Hz), 7.56-7.49 (3H, m), 7.37-7.33 (4H, m), 7.31-7.26 (1H, m), 6.52 (1H, d, J=5.2 Hz), 4.23 (1H, d, J=13.2 Hz), 4.10-3.98 (1H, br), 4.00 (3H, s), 3.83 (2H, s), 3.78 (1H, d, J=14.4 Hz), 3.21-3.15 (2H, m), 2.78 (1H, t, J=10.8 Hz), 2.68-2.65 (1H, m), 2.00 (3H, s), 1.93-1.88 (1H, m), 1.86-1.81 (1H, m); ESI-MS m/z 630 (MH$^+$).

Example 19 tert-Butyl 4-(2-fluoro-4-(3-(2-(4-fluorophenyl)acetyl)thioureido)phenoxy)-7-methoxyquinoline-6-carboxylate (19a)

4-Fluorophenylacetic acid (900 mg) was dissolved in thionyl chloride (5 mL), and the solution was refluxed under heating for 2 hours. The reaction system was concentrated under reduced pressure and azeotroped with toluene, to thereby yield 4-fluorophenylacetyl chloride as a crude product. This acid chloride was dissolved in acetonitrile (20 mL), and potassium thioisocyanate (851 mg) was added to the solution, followed by stirring at 70° C. for 5 hours. The reaction mixture was cooled to room temperature and concentrated under reduced pressure. Subsequently, the product was separated with saturated aqueous solution of sodium hydrogencarbonate (100 mL) and ethyl acetate (50 mL). The organic layer was washed with saturated brine (100 mL) and dried over sodium sulfate, followed by concentration under reduced pressure, to thereby yield 4-fluorophenylacetyl thioisocyanate. This thioisocyanate was not subjected to further purification and dissolved in tetrahydrofuran (20 mL). A solution (20 mL) of compound 1c (374 mg) in tetrahydrofuran was added to the thioisocyanate solution and the mixture was stirred at room temperature for 12 hours. The reaction mixture was concentrated under reduced pressure, and the formed solid was filtrated, to thereby yield compound 19a (452 mg, yield: 79%).

$^1$H-NMR (CDCl$_3$) δ: 12.47 (1H, s), 11.82 (1H, s), 8.73 (1H, s), 8.65 (1H, d, J=4.4 Hz), 7.95 (1H, dd, J=11.2 Hz, 2.8 Hz), 7.49 (1H, s), 7.43-7.40 (1H, m), 7.31-7.25 (3H, m), 7.15 (2H, m), 6.42 (1H, dd, J=5.2 Hz, 1.2 Hz), 4.03 (3H, s), 3.74 (2H, s), 1.64 (9H, s); ESI-MS m/z 580 (MH$^+$).

4-(2-Fluoro-4-(3-(2-(4-fluorophenyl)acetyl)thioureido)phenoxy)-7-methoxyquinoline-6-carboxylic acid hydrochloride (19b)

Compound 19a (385 mg) was dissolved in 4N HCl-dioxane solution (10 mL), and the solution was stirred at 80° C. for 4 hours. The precipitate in the reaction mixture was filtrated, to thereby yield compound 19b (245 mg, yield: 66%).

1H-NMR (DMSO-d$_6$) δ: 12.52 (1H, s), 11.85 (1H, s), 8.94 (1H, d, J=6.0 Hz), 8.68 (1H, s), 8.11 (1H, d, J=12.4 Hz), 7.66 (1H, s), 7.62 (1H, d, J=3.4 Hz), 7.39 (2H, dd, J=8.4 Hz, 5.6 Hz), 7.19 (2H, t, J=8.8 Hz), 6.85 (1H, d, J=6.0 Hz), 4.04 (3H, s), 3.84 (2H, s); ESI-MS m/z 524 (MH$^+$).

4-(2-Fluoro-4-(3-(2-(4-fluorophenyl)acetyl)thioureido)phenoxy)-7-methoxy-N-(2-oxoazepan-3-yl)quinoline-6-carboxamide (19)

Similar to the synthesis of Example 1, from compound 19b (53.0 mg), DL-α-amino-ε-caprolactam (14.3 mg), triethylamine (38.9 μL), and DMTMM•n-hydrate (30.9 mg), the titled compound 19 was yielded (16.9 mg, yield: 29%).

$^1$H-NMR (DMSO-d$_6$) δ: 12.47 (1H, s), 11.81 (1H, s), 9.20 (1H, d, J=5.6 Hz), 8.90 (1H, s), 8.71 (1H, d, J=5.2 Hz), 8.04-7.96 (2H, m), 7.60 (1H, s), 7.57-7.51 (2H, m), 7.39-7.36 (2H, m), 7.20-7.15 (2H, m), 6.53 (1H, d, J=5.2 Hz), 4.65-4.61 (1H, m), 4.10 (3H, s), 3.83 (2H, s), 3.48-3.44 (2H, m), 2.08-2.05 (1H, m), 1.94-1.90 (1H, m), 1.79-1.72 (2H, m), 1.44-1.40 (1H, m), 1.29-1.19 (1H, m)

Example 20

(S)-tert-Butyl 2-(3-fluoropyrrolidin-1-yl)-2-oxoethylcarbamate (20a)

(S)-3-Fluoropyrrolidine hydrochloride (535 mg), N-Boc glycine (746 mg), 1-ethyl-3-(3-dimethylaminopropyl)carbodiimide hydrochloride (1.41 g), 1-hydroxybenzotriazole (993 mg), and triethylamine (1.19 mL) were dissolved in tetrahydrofuran (5 mL), and the solution was stirred at 70° C. for 1 hour. The reaction mixture was concentrated under reduced pressure, and aqueous saturated sodium bicarbonate (20 mL) was added to the residue, followed by extraction with ethyl acetate (10 mL). The organic layer was washed sequentially with 0.1N HCl (10 mL) and saturated brine (10 mL) and dried over sodium sulfate, followed by concentration under reduced pressure, to thereby yield compound 20a (98.1 mg, yield: 9.3%).

$^1$H-NMR (CDCl$_3$) δ: 5.45 (1H, br), 5.40-5.19 (1H, m), 4.00-3.82 (3H, m), 3.72-3.49 (3H, m), 4.10 (3H, s), 3.83 (2H, s), 3.48-3.44 (2H, m), 2.41-2.24 (1H, m), 2.19-1.91 (1H, m); FAB-MS m/z 247 (MH$^+$).

(S)-2-Amino-1-(3-fluoropyrrolidin-1-yl)ethanone hydrochloride (20b)

Compound 20a (98.1 mg) was dissolved in 4N HCl-1,4-dioxane solution, and the solution was stirred at room temperature for 4 hours, to thereby yield compound 20b (33.5 mg, yield: 46%).

$^1$H-NMR (DMSO-d$_6$) δ: 8.28 (3H, br), 5.48-5.22 (1H, m), 3.88-3.27 (6H, m), 2.29-1.89 (2H, m)

(S)-4-(2-Fluoro-4-(3-(2-phenylacetyl)thioureido)phenoxy)-N-(2-(3-fluoropyrrolidin-1-yl)-2-oxoethyl)-7-methoxyquinoline-6-carboxamide (20)

Similar to the synthesis of Example 1, from compound 1e (35.3 mg), compound 20b (14.3 mg), triethylamine (22.7 μL), and DMTMM•n-hydrate (21.6 mg), the titled compound 20 was yielded (15.1 mg, yield: 37%).

$^1$H-NMR (DMSO-d$_6$) δ: 12.50 (1H, s), 11.82 (1H, s), 8.83 (1H, t, J=4.4 Hz), 8.81 (1H, s), 8.71 (1H, d, J=5.2 Hz), 7.59 (1H, s), 7.57-7.51 (2H, m), 7.37-7.33 (5H, m), 7.31-7.25 (1H, m), 6.53 (1H, d, J=5.6 Hz), 5.49-27 (1H, m), 4.27-4.13 (2H, m), 4.08 (3H, s), 3.82 (2H, s), 3.86-3.63 (3H, m), 2.32-2.05 (3H, m); ESI-MS m/z 634 (MH$^+$).

Example 21

4-(2-Fluoro-4-(3-(2-phenylacetyl)thioureido)phenoxy)-7-methoxy-N-(2-morpholino-2-oxoethyl)quinoline-6-carboxamide (21)

Similar to the synthesis of Example 1, from compound 1e (24.2 mg), 2-amino-1-morpholinoethanone hydrochloride (synthesized according to J. Med. Chem., 1988, 31 (11), 2145-2152) (9.67 mg), triethylamine (18.7 μL), and DMTMM•n-hydrate (14.8 mg), the titled compound 21 was yielded (18.4 mg, yield: 65%).

$^1$H-NMR (DMSO-d$_6$) δ: 12.50 (1H, s), 11.82 (1H, s), 8.85-8.83 (1H, m), 8.82 (1H, s), 8.71 (1H, dd, J=5.2 Hz), 8.03 (1H, d, J=12.0 Hz), 7.60 (1H, s), 7.55 (1H, s), 7.55-7.50 (1H, m), 7.35-7.28 (5H, m), 6.52 (1H, d, J=5.2 Hz), 4.24 (2H, d, J=4.8 Hz), 4.08 (2H, s), 3.96 (3H, s), 3.82 (2H, s), 3.59 (2H, d, J=13.2 Hz), 3.53-3.48 (2H, m), 3.15-3.00 (2H, m); ESI-MS m/z 632 (MH$^+$).

Example 22

N-(2-(Dimethylamino)-2-oxoethyl)-4-(2-fluoro-4-(3-(2-phenylacetyl)thioureido)phenoxy)-7-methoxyquinoline-6-carboxamide (22)

Similar to the synthesis of Example 1, from compound 1e (37.0 mg), 2-amino-N,N-dimethylacetamide hydrochloride (11.4 mg), DMTMM•n-hydrate (22.7 mg), and triethylamine (23.8 μL), the titled compound 22 was yielded (6.8 mg, yield: 17%).

$^1$H-NMR (DMSO-d$_6$) δ: 12.51 (1H, s), 11.82 (1H, s), 8.87-8.84 (2H, m), 8.72 (1H, dd, J=5.4 Hz, 0.6 Hz), 7.60-7.52 (3H, m), 7.38-7.33 (4H, m), 7.31-7.26 (1H, m), 6.54 (1H, d, J=4.8 Hz), 4.21 (2H, d, J=4.8 Hz), 4.09 (3H, s), 3.83 (2H, s), 3.00 (3H, s), 2.89 (3H, m); ESI-MS m/z 590 (MH$^+$).

Example 23

4-(2-Fluoro-4-(3-(2-(4-fluorophenyl)acetyl)thioureido)phenoxy)-N-(2-hydroxybutyl)-7-methoxyquinoline-6-carboxamide (23)

Similar to the synthesis of Example 1, from compound 19b (25.0 mg), 1-amino-2-butanol (10.6 μL), and DMTMM•n-hydrate (14.8 mg), the titled compound 23 was yielded (14.2 mg, yield: 53%).

$^1$H-NMR (DMSO-d$_6$) δ: 12.47 (1H, s), 11.81 (1H, s), 8.69 (1H, d, J=4.0 Hz), 8.65 (1H, s), 8.39 (1H, t, J=8.8 Hz), 8.02

(1H, d, J=11.2 Hz), 7.55-7.49 (3H, m), 7.37 (2H, dd, J=7.0 Hz, 6.0 Hz), 7.17 (2H, t, J=8.8 Hz), 6.52 (1H, d, J=5.4 Hz), 4.80 (1H, d, J=4.8 Hz), 4.03 (3H, s), 3.86 (2H, s), 3.82 (2 H, s), 1.51-1.45 (2H, m), 1.39-1.31 (2H, m), 0.90 (3H, t, J=7.2 Hz); ESI-MS m/z 595 (MH$^+$).

Example 24

4-(2-Fluoro-4-(3-(2-phenylacetyl)thioureido)phenoxy)-N-(2-hydroxy-2-methylpropyl)-7-methoxyquinoline-6-carboxamide (24)

Similar to the synthesis of Example 1, from compound 1e (49.1 mg), 1-amino-2-methylpropan-2-ol (synthesized according to Angew. Chem. Int. Ed., 2007, 46 (25), 4751-4753) (20.2 mg), and DMTMM•n-hydrate (30.1 mg), the titled compound 24 was yielded (36.1 mg, yield: 69%).
$^1$H-NMR (DMSO-d$_6$) δ: 12.50 (1H, s), 11.80 (1H, s), 8.69 (1H, d, J=5.6 Hz), 8.66 (1H, s), 8.34 (1H, t, J=6.0 Hz), 8.02 (1H, d, J=11.2 Hz), 7.57-7.52 (3H, m), 7.37-7.33 (4H, m), 7.30-7.27 (1H, m), 6.52 (1H, d, J=5.6 Hz), 4.63 (1H, s), 4.04 (3H, s), 3.83 (2H, s), 3.81 (1H, d, J=2.4 Hz), 1.55 (1H, s), 1.14 (6H, s); ESI-MS m/z 577 (MH$^+$)

Example 25

4-(2-Fluoro-4-(3-(2-phenylacetyl)thioureido)phenoxy)-N-((1-hydroxycyclohexyl)methyl)-7-methoxyquinoline-6-carboxamide (25)

Similar to the synthesis of Example 1, from compound 1e (17.9 mg), 1-(aminomethyl)cyclohexanol hydrochloride (synthesized according to J. Org. Chem., 1989. 54 (24), 5651-5654) (6.57 mg), and DMTMM•n-hydrate (11.0 mg), the titled compound 25 was yielded (8.2 mg, yield: 40%).
$^1$H-NMR (CDCl$_3$) δ: 12.51 (1H, s), 9.25 (1H, s), 8.66 (1H, d, J=5.2 Hz), 8.55 (1H, s), 8.23 (1H, t, J=5.4 Hz), 7.96 (1H, dd, J=11.6 Hz, 2.4 Hz), 7.53 (1H, s), 7.46-7.37 (4H, m), 7.33-7.23 (3H, m), 6.44 (1H, dd, J=5.2 Hz, 0.8 Hz), 4.12 (3H, s), 3.76 (2H, s), 3.58 (1H, d, J=5.8 Hz), 1.65-1.52 (10H, m), 1.37 (1H, br); ESI-MS m/z 617 (MH$^+$).

Example 26

4-(2-Fluoro-4-(3-(2-phenylacetyl)thioureido)phenoxy)-N-((4-hydroxytetrahydro-2H-pyran-4-yl)methyl)-7-methoxyquinoline-6-carboxamide (26)

Similar to the synthesis of Example 1, from compound 1e (241 mg), 4-(aminoethyl)tetrahydro-2H-pyran-4-ol hydrochloride (synthesized according to US 2005/0696358 A1) (89.4 mg), triethylamine (155 μL), and DMTMM•n-hydrate (147 mg), the titled compound 26 was yielded (236 mg, yield: 86%).
$^1$H-NMR (CDCl$_3$) δ: 12.51 (1H, s), 9.26 (1H, s), 8.67 (1H, d, J=5.4 Hz), 8.45 (1H, s), 8.26 (1H, t, J=6.0 Hz), 7.96 (1H, d, J=11.6 Hz, 2.4 Hz), 7.55 (1H, s), 7.47-7.38 (4H, m), 7.33-7.24 (3H, m), 6.52 (1H, dd, J=5.2 Hz, 0.8 Hz), 4.13 (3H, s), 3.83-3.78 (4H, m), 3.76 (2H, s), 3.61 (2H, d, J=6.4 Hz), 3.30 (1H, br), 1.78 (2H, m), 1.64 (2H, d, J=12.8 Hz); ESI-MS m/z 619 (MH$^+$).

Example 27

4-(2-Fluoro-4-(3-(2-phenylacetyl)thioureido)phenoxy)-7-methoxy-N-(2-(methylsulfonyl)ethyl)quinoline-6-carboxamide (27)

Similar to the synthesis of Example 1, compound 1e (25 mg), 2-(methylsulfonyl)ethaneamine (6 mg), triethylamine (19 μL), and DMTMM•n-hydrate (20 mg) were dissolved in ethanol (1 mL), and the solution was stirred at room temperature for 1 hour, to thereby yield the titled compound 27 (20.6 mg, yield: 73%).
$^1$H-NMR (DMSO-d$_6$) δ: 12.50 (1H, s), 11.83 (1H, s), 8.77 (1H, t, J=5.6 Hz), 8.70-8.69 (2H, m), 8.03 (1H, dd, J=12.2 Hz, 1.8 Hz), 7.57-7.50 (4H, m), 7.38-7.34 (4H, m), 7.31-7.26 (1H, m), 6.53 (1H, d, J=5.6 Hz), 4.03 (3H, s), 3.83 (2H, s), 3.76 (2H, d t, J=6.2 Hz), 3.42 (2H, d, J=6.8 Hz), 3.07 (3H, s); ESI-MS m/z 611 (MH$^+$).

Example 28

4-(2-Fluoro-4-(3-(2-phenylacetyl)thioureido)phenoxy)-7-methoxy-N-o-tolylquinoline-6-carboxamide (28)

Similar to the synthesis of compound 1, from compound 1e (32 mg), o-toluidine (7.59 μL), and DMTMM•n-hydrate (19.6 mg), the titled compound 28 was yielded (19.8 mg, yield: 56%).
$^1$H-NMR (400 Hz, DMSO-d$_6$) δ: 12.51 (1H, s), 11.82 (1H, s), 9.96 (1H, s), 8.76 (1H, s), 8.72 (2H, d, J=5.2 Hz), 7.64 (1H, s), 7.81 (1H, d, J=7.2 Hz), 7.58-7.52 (2H, m), 7.36-7.33 (4H, m), 7.30-7.21 (3H, m), 7.12 (1H, t, J=7.6 Hz), 6.55 (1H, d, J=5.6 Hz), 4.12 (3H, s), 3.83 (2H, s), 2.34 (3H, s); ESI-MS m/z 595 (MH$^+$)

Example 29

(S)-4-(2-Fluoro-4-(3-(2-phenylacetyl)thioureido) phenoxy)-N-(2-hydroxy-1-phenylethyl)-7-methoxyquinoline-6-carboxamide (29)

Similar to the synthesis of compound 1, from compound 1e (44 mg), (S)-2-amino-2-phenylethanol (15.5 mg), and DMTMM•n-hydrate (19.1 mg), the titled compound 29 was yielded (47.0 mg, yield: 86%).
$^1$H-NMR (400 Hz, DMSO-d$_6$) δ: 12.50 (1H, s), 11.82 (1H, s), 8.83 (1H, d, J=8.0 Hz), 8.69 (1H, d, J=5.2 Hz), 8.58 (1H, s), 8.02 (1H, dd, J=11.6 Hz, 1.6 Hz), 7.57 (1H, s), 7.57-7.49 (2H, m), 7.41-7.31 (7H, m), 7.29-7.22 (3H, m), 6.52 (1H, d, J=5.2 Hz), 5.09 (1H, q, J=7.6 Hz), 5.02 (1H, t, J=5.6 Hz), 4.06 (3H, s), 3.82 (2H, s), 3.70-3.67 (2H, m); ESI-MS m/z 625 (MH$^+$)

Example 30

4-(2-Fluoro-4-(3-(2-phenylacetyl)thioureido)phenoxy)-N-(2-hydroxy-2-(2-methyl-2H-tetrazol-5-yl) ethyl)-7-methoxyquinoline-6-carboxamide (30)

Similar to the synthesis of compound 1, from compound 1e (30.0 mg), 2-amino-1-(2-methyl-2H-tetrazol-5-yl)ethanol (12.7 mg), and DMTMM•n-hydrate (19.7 mg), the titled compound 30 was yielded (31.2 mg, yield: 83%).
$^1$H-NMR (400 Hz, DMSO-d$_6$) δ: 12.50 (1H, s), 11.82 (1H, s), 8.68 (1H, d, J=5.2 Hz), 8.64 (1H, s), 8.58-8.53 (1H, m), 8.03 (1H, d, J=11.6 Hz), 7.57-7.52 (3H, m), 7.36-7.33 (4H, m), 7.30-7.26 (1H, m), 6.52 (1H, d, J=5.6 Hz), 6.07 (1H, d, J=6.4 Hz), 4.34 (3H, s), 4.00 (3H, s), 3.83-3.82 (3H, m), 3.78-3.70 (2H, m); ESI-MS m/z 649 (MH$^+$)

Example 31

(S)-4-(2-Fluoro-4-(3-(2-phenylacetyl)thioureido)phenoxy)-N-(1-hydroxybutan-2-yl)-7-methoxyquinoline-6-carboxamide (31)

Similar to the synthesis of compound 1, from compound 1e (81.7 mg), (S)-2-aminobutan-1-ol (22.8 μL), and DMTMM•n-hydrate (53.7 mg), the titled compound 31 was yielded (89.6 mg, yield: 96%).
$^1$H-NMR (400 Hz, DMSO-d$_6$) δ: 12.50 (1H, s), 11.82 (1H, s), 8.68 (1H, d, J=5.1 Hz), 8.55 (1H, s), 8.12 (1H, d, J=8.6 Hz), 8.02 (1H, dd, J=12.0 Hz, 1.4 Hz), 7.58-7.48 (3H, m), 7.36-7.25 (4H, m), 7.31-7.25 (1H, m), 6.51 (1H, d, J=5.4 Hz), 4.75 (1H, t, J=5.6 Hz), 4.01 (3H, s), 3.92-3.85 (1H, m), 3.82 (2H, s), 3.52-3.47 (1H, m), 3.45-3.38 (1H, m), 1.78-1.70 (1H, m), 1.50-1.40 (1H, m), 0.92 (3H, t, J=7.6 Hz); ESI-MS m/z 577 (MH$^+$)

Example 32

4-(2-Fluoro-4-(3-(2-phenylacetyl)thioureido)phenoxy)-N-(1-hydroxytetrahydrothiophen-3-yl)-7-methoxyquinoline-6-carboxamide (32)

Similar to the synthesis of compound 1, from compound 1e (25.7 mg), 4-aminotetrahydrothiophen-3-ol hydrochloride (16.9 mg), DMTMM•n-hydrate (11.5 mg), and triethylamine (14.2 μL), the titled compound 32 was yielded (30.2 mg, yield: 93%).
$^1$H-NMR (400 Hz, DMSO-d$_6$) δ: 12.50 (1H, s), 11.82 (1H, s), 8.81 (1H, s), 8.71 (1H, d, J=5.2 Hz), 8.57 (1H, d, J=7.2 Hz), 8.03 (1H, dd, J=13.2 Hz, 2.4 Hz), 7.58 (1H, s), 7.57-7.50 (2H, m), 7.36-7.25 (5H, m), 6.54 (1H, dd, J=5.2 Hz, 0.8 Hz), 4.37 (2H, d, J=4.8 Hz), 4.06 (3H, s), 3.83 (2H, s), 3.10 (1H, dd, J=12.0 Hz, 4.4 Hz), 3.02 (1H, dd, J=9.6 Hz, 7.2 Hz), 2.80-2.62 (3H, m); ESI-MS m/z 625 (MH$^+$)

Example 33 tert-Butyl 2-(4-(2-fluoro-4-(3-(2-phenylacetyl)thioureido)phenoxy)-7-methoxyquinoline-6-carboxamido)acetate (33a)

Similar to the synthesis of compound 1, from compound 1e (65.2 mg), glycine tert-butyl ester hydrochloride (18.9 mg), DMTMM•n-hydrate (39.9 mg), and triethylamine (42.1 μL), compound 33a was yielded (67.2 mg, yield: 90%).
$^1$H-NMR (400 Hz, CDCl$_3$) δ: 12.51 (1H, s), 9.28 (1H, d, J=4.8 Hz), 8.66 (1H, d, J=5.6 Hz), 8.59 (1H, br), 8.51 (1H, dd, J=4.8 Hz), 7.95 (1H, dd, J=12.0 Hz, 2.4 Hz), 7.46-7.36 (5H, m), 7.32-7.23 (3H, m), 6.44 (1H, d, J=4.8 Hz, 1.2 Hz), 4.24 (2H, d, J=4.8 Hz), 4.16 (3H, s), 3.76 (2H, s), 1.53 (9H, s); ESI-MS m/z 619 (MH$^+$)

2-(4-(2-Fluoro-4-(3-(2-phenylacetyl)thioureido)phenoxy)-7-methoxyquinoline-6-carboxamido)acetic acid hydrochloride (33b)

Similar to the synthesis of compound 1e, from compound 33a (55.7 mg), compound 33b was yielded (37.2 mg, yield: 63%).
$^1$H-NMR (400 Hz, DMSO-d$_6$) δ: 12.55 (1H, s), 11.86 (1H, s), 8.98 (1H, d, J=6.0 Hz), 8.87 (1H, dd, J=5.6 Hz), 8.76 (1H, s), 8.12 (1H, dd, J=12.4 Hz, 1.2 Hz), 7.74 (1H, s), 7.64-7.62 (2H, m), 7.36-7.34 (5H, m), 7.32-7.27 (1H, m), 6.91 (1H, d, J=6.4 Hz), 4.09 (3H, s), 4.01 (2H, d, J=5.6 Hz), 3.83 (2H, s); ESI-MS m/z 563 (MH$^+$)

4-(2-Fluoro-4-(3-(2-phenylacetyl)thioureido)phenoxy)-7-methoxy-N-(2-(2-methoxyethylamino)-2-oxoethyl)quinoline-6-carboxamide (33)

Similar to the synthesis of compound 1, from compound 33b (50 mg), 2-methoxyethaneamine (11 μL), DMTMM•n-hydrate (34.6 mg), and N-methylmorpholine (18.4 μL), the titled compound 33 was yielded (12.0 mg, yield: 23%).
$^1$H-NMR (400 Hz, DMSO-d$_6$) δ: 12.51 (1H, s), 11.83 (1H, s), 8.76 (1H, s), 8.75 (1H, t, J=5.4 Hz), 8.71 (1H, d, J=5.4 Hz), 8.06-8.00 (2H, m), 7.59 (1H, s), 7.57-7.50 (2H, m), 7.38-7.26 (5H, m), 6.53 (1H, d, J=5.4 Hz), 4.07 (3H, s), 3.97 (2H, d, J=5.4 Hz), 3.84 (2H, s), 3.39-3.35 (2H, m), 3.30-3.27 (2H, m), 3.25 (3H, s); ESI-MS m/z 620 (MH$^+$)

Example 34

(S)-4-(2-Fluoro-4-(3-(2-phenylacetyl)thioureido)phenoxy)-N-(2-(2-(hydroxymethyl)pyrrolidin-1-yl)-2-oxoethyl)-7-methoxyquinoline-6-carboxamide (34)

Similar to the synthesis of compound 1, from compound 33b (50 mg), (S)-pyrrolidin-2-ylmethanol (11 μL), DMTMM•n-hydrate (30 mg), and N-methylmorpholine (24 μL), the titled compound 34 was yielded (32 mg, yield: 60%).
$^1$H-NMR (400 Hz, DMSO-d$_6$) δ: 12.51 (1H, brs), 11.83 (1H, brs), 8.88-8.83 (2H, m), 8.72 (1H, d, J=5.1 Hz), 8.04 (1H, d, J=12.2 Hz), 7.63-7.51 (3H, m), 7.39-7.26 (5H, m), 6.54 (1H, d, J=5.1 Hz), 4.74 (1H, t, J=5.5 Hz), 4.39-4.22 (1H, m), 4.18-4.13 (1H, m), 4.10 (3H, s), 4.05-3.95 (1H, m), 3.84 (2H, s), 3.56-3.41 (3H, m), 2.02-1.76 (5H, m); ESI-MS m/z 646 (MH$^+$)

Example 35

N-(2-(Ethyl(2-hydroxy-2-methylpropyl)amino)-2-oxoethyl)-4-(2-fluoro-4-(3-(2-phenylacetyl)thioureido)phenoxy)-7-methoxyquinoline-6-carboxamide (35)

Similar to the synthesis of compound 1, from compound 33b (35.0 mg), 1-(ethylamino)-2-methylpropan-2-ol (17.1 mg), and DMTMM•n-hydrate (19.4 mg), the titled compound 35 was yielded (12.3 mg, yield: 32%).
$^1$H-NMR (400 Hz, DMSO-d$_6$) δ: 12.50 (1H, s), 11.82 (1H, s), 8.86 (1H, sbr), 8.84 (1H, d, J=2.7 Hz), 8.71 (1H, d, J=5.4 Hz), 8.03 (1H, dd, J=11.7 Hz, 2.0 Hz), 7.59 (1 H, s), 7.57-7.52 (2H, m), 7.37-7.32 (4H, m), 7.21-7.25 (1H, m), 6.53 (1H, d, J=5.6 Hz), 4.32-4.27 (2H, m), 4.09, 4.07 (3H, s), 3.82 (2H, s), 3.50-3.20 (4H, m), 1.18-1.13 (5H, m), 1.09-1.01 (5H, m); ESI-MS m/z 662 (MH$^+$)

Example 36 tert-Butyl 2-(4-(2-fluoro-4-(3-(2-phenylacetyl)thioureido)phenoxy)-7-methoxyquinoline-6-carboxamido)propanoate (36a)

Similar to the synthesis of compound 1, from compound 1e (100 mg), alanine tert-butyl ester hydrochloride (47 mg), and DMTMM•n-hydrate (71 mg), compound 36a was yielded (109 mg, yield: 87%).

¹H-NMR (400 Hz, DMSO-$d_6$) δ: 12.57 (1H, s), 11.89 (1H, s), 8.76 (1H, d, J=5.2 Hz), 8.65 (1H, s), 8.61 (1H, t, J=5.2 Hz), 8.10 (1H, d, J=12.4 Hz), 7.60-7.30 (8H, m), 6.60 (1H, d, J=5.2 Hz), 4.08 (3H, s), 3.90 (2H, s), 3.57 (2H, td, J=6.5 Hz, J=6.5 Hz), 2.57 (2H, t, J=6.5 Hz), 1.47 (9H, s); ESI-MS m/z 633 (MH⁺)

2-(4-(2-Fluoro-4-(3-(2-phenylacetyl)thioureido)phenoxy)-7-methoxyquinoline-6-carboxamido)propanoic acid hydrochloride (36b)

Similar to the synthesis of compound 1e, from compound 36a (95 mg), compound 36b was yielded (92 mg, yield: 100%).

¹H-NMR (400 Hz, DMSO-$d_6$) δ; 12.55 (1H, s), 11.86 (1H, s), 8.94 (1H, d, J=5.9 Hz), 8.68 (1H, s), 8.65 (1H, t, J=5.9 Hz), 8.11 (1H, d, J=12.4 Hz), 7.69-7.58 (3H, m), 7.38-7.25 (5H, m), 6.87 (1H, d, J=5.9 Hz), 4.05 (3H, s), 3.84 (2H, s), 3.54 (2H, td, J=6.7 Hz, J=6.7 Hz), 2.55 (2H, t, J=6.7 Hz); ESI-MS m/z 577 (MH⁺)

N-(3-(Dimethylamino)-3-oxopropyl)-4-(2-fluoro-4-(3-(2-phenylacetyl)thioureido)phenoxy)-7-methoxyquinoline-6-carboxamide (36)

Similar to the synthesis of Example 1, from compound 36b (30 mg), dimethylamine hydrochloride (6.0 mg), DMTMM•n-hydrate (20 mg), and N-methylmorpholine (16 μL), the titled compound 36 was yielded (21.2 mg, yield: 68%).

¹H-NMR (400 Hz, DMSO-$d_6$) δ: 12.51 (1H, s), 11.83 (1H, s), 8.72 (1H, s) 8.70 (1H, d, J=5.2 Hz), 8.66 (1H, t, J=5.9 Hz), 8.04 (1H, d, J=12.2 Hz), 7.58-7.25 (8H, m), 6.53 (1H, d, J=5.2 Hz), 4.04 (3H, s), 3.84 (2H, s), 3.54 (2H, td, J=6.4 Hz, J=6.4 Hz), 2.97 (3H, s), 2.85 (3H, s), 2.61 (2H, t, J=6.4 Hz); ESI-MS m/z 604 (MH⁺)

Example 37

4-(2-fluoro-4-(3-(2-(4-fluorophenyl)acetyl)thioureido)phenoxy)-7-methoxy-N-(2-morpholinoethyl)quinoline-6-carboxamide (37)

Similar to the synthesis of Example 1, from compound 19b (523 mg), 2-morpholinoethaneamine (171 mg), and DMTMM•n-hydrate (360 mg), the titled compound 37 was yielded (462 mg, yield: 73%).

¹H-NMR (400 Hz, DMSO-$d_6$) δ: 12.47 (1H, s), 11.82 (1H, s), 8.70 (1H, d, J=5.2 Hz), 8.70 (1H, s) 8.53-8.48 (1H, m), 8.02 (1H, d, J=13.0 Hz), 7.59-7.48 (3H, m), 7.43-7.33 (2H, m), 7.24-7.13 (2H, m), 6.53 (1H, d, J=5.2 Hz), 4.07 (3H, s), 3.84 (2H, s), 3.63-3.59 (4H, m), 3.49-3.32 (6H, m), 2.50-2.40 (2H, m); ESI-MS m/z 636 (MH⁺)

Example 38

(S)-4-(2-Fluoro-4-(3-(2-(4-fluorophenyl)acetyl)thioureido)phenoxy)-N-(1-hydroxybutan-2-yl)-7-methoxyquinoline-6-carboxamide (38)

Similar to the synthesis of Example 1, from compound 19b (50 mg), (S)-2-aminobutan-1-ol (12 μL), and DMTMM•n-hydrate (34 mg), the titled compound 38 was yielded (25 mg, yield: 45%).

¹H-NMR (400 Hz, DMSO-$d_6$) δ: 12.48 (1H, sbr), 11.82 (1H, sbr), 8.69 (1H, d, J=5.2 Hz), 8.57 (1H, s), 8.13 (1H, d, J=8.3 Hz), 8.03 (1H, d, J=13.2 Hz), 7.58-7.50 (3H, m), 7.39 (2H, dd, J=8.5 Hz, J=5.6 Hz), 7.22-7.15 (2H, m), 6.52 (1H, d, J=5.2 Hz), 4.77 (1H, t, J=5.6 Hz), 4.03 (3H, s), 3.93-3.86 (1H, m), 3.84 (2H, s), 3.55-3.48 (1H, m), 3.45-3.40 (1H, m), 1.72-1.63 (1H, m), 1.53-1.42 (1H, m), 0.93 (3H, t, J=7.4 Hz); ESI-MS m/z 595 (MH⁺)

Example 39

Methyl 4-(2-fluoro-4-nitrophenoxy)-7-methoxyquinoline-6-carboxylate (39a)

From methyl 4-chloro-7-methoxyquinoline-6-carboxylate (synthesized according to WO 2005/080377) (1.00 g), 2-fluoro-4-nitrophenol (936 mg), and N,N-diisopropylethylamine (1.35 mL), compound 39a was yielded (1.38 g, yield: 93%).

¹H-NMR (CDCl₃) δ: 8.74 (1H, s), 8.73 (1H, d, J=5.2 Hz), 7.54 (1H, s), 7.45-7.40 (3H, m), 6.49 (1H, dd, J=5.0 Hz, 1.4 Hz), 4.06 (3H, s), 3.98 (3H, s); ESI-MS m/z 373 (MH⁺).

Methyl 4-(4-amino-2-fluorophenoxy)-7-methoxyquinoline-6-carboxylate (39b)

Similar to the synthesis of compound 1b, from compound 39a (275 mg), iron powder (206 mg), and ammonium chloride (275 mg), compound 39b was yielded (188 mg, yield: 74%).

¹H-NMR (400 Hz, CDCl₃) δ: 8.83 (1H, s), 8.63 (1H, d, J=5.2 Hz), 7.48 (1H, s), 7.03 (1H, t, J=8.4 Hz), 6.56 (1H, dd, J=11.6 Hz, 2.8 Hz), 6.50 (1H, ddd, J=8.8 Hz, 2.6 Hz, 1.0 Hz), 6.41 (1H, dd, J=5.0 Hz, 1.2 Hz), 4.04 (3H, s), 3.97 (3H, s), 3.84 (2H, sbr); ESI-MS m/z 343 (MH⁺)

4-(4-Amino-2-fluorophenoxy)-7-methoxyquinoline-6-carboxylic acid (39c)

Compound 39b (1.0 g) was added to methanol (10 mL), and 4M aqueous sodium hydroxide (650 μL) and water (400 μL) were further added thereto, followed by stirring at room temperature for 2 hours. After completion of reaction, 6N aqueous hydrochloric acid was added to the reaction mixture, to thereby adjust the pH to 3, and the precipitate was filtrated, whereby compound 39c was yielded (862 mg, yield: 90%).

¹H-NMR (400 Hz, DMSO-$d_6$) δ: 8.66 (1H, d, J=5.4 Hz), 8.54 (1H, s), 7.48 (1H, s), 7.09 (1H, dd, J=8.8 Hz), 6.55 (1H, dd, J=13.0 Hz, 2.7 Hz), 6.48-6.43 (2H, m), 5.55 (1H, sbr), 3.96 (3H, s); ESI-MS m/z 329 (MH⁺)

4-(4-(3-(2-(2-Fluorophenyl)acetylthioureido)-2-fluorophenoxy)-7-methoxyquinoline-6-carboxylic acid (39d)

Similar to the synthesis of compound 1d, from compound 39c (1.79 g), 2-fluorophenylacetyl thioisocyanate (1.97 g), and a solvent mixture of N,N-dimethylacetamide (30 mL), toluene (30 mL), and ethanol (6 mL), carboxylic acid 39d was yielded as a crude product (1.89 g, yield: 89%). The crude product was employed in a subsequent reaction without further purification.

4-(2-Fluoro-4-(3-(2-(2-fluorophenyl)acetyl)thioureido)phenoxy)-N-(2-hydroxy-2-methylpropyl)-7-methoxyquinoline-6-carboxamide (39)

Similar to the synthesis of compound 1, from compound 39d (126 mg), DMTMM•n-hydrate (87 mg), and 1-amino-2-methylpropan-2-ol (37 mg), the titled compound 39 was yielded (89 mg, yield: 62%).

¹H-NMR (400 Hz, CDCl₃) δ: 12.43 (1H, s), 9.26 (1H, s), 8.67 (1H, d, J=5.1 Hz), 8.59 (1H, m), 8.26 (1H, m), 7.97 (1H, dd, J=11.5 Hz, 2.4 Hz), 7.54 (1H, s), 7.44-7.15 (6H, m), 6.44 (1H, dd, J=5.4 Hz, 1.2 Hz), 4.13 (3H, s), 3.79 (2H, s), 3.57 (2H, d, J=5.8 Hz), 2.57 (1H, s), 1.33 (6H, s); ESI-MS m/z 595 (MH⁺)

Example 40

(S)-4-(2-Fluoro-4-(3-(2-(2-fluorophenyl)acetyl)thioureido)phenoxy)-N-(1-hydroxybutan-2-yl)-7-methoxyquinoline-6-carboxamide (40)

Similar to the synthesis of compound 1, from compound 39d (121 mg), DMTMM•n-hydrate (83 mg), and (S)-2-aminobutan-1-ol (28 mg), the titled compound 40 was yielded (84 mg, yield: 61%).
¹H-NMR (400 Hz, CDCl₃) δ: 12.44 (1H, s), 9.25 (1H, s), 8.67 (1H, d, J=5.1 Hz), 8.64 (1H, s), 8.03 (1H, d, J=7.6 Hz), 7.97 (1H, dd, J=11.6 Hz, 2.6 Hz), 7.54 (1H, s), 7.44-7.14 (6H, m), 6.45 (1H, dd, J=5.1 Hz, 1.2 Hz), 4.12 (3H, s), 3.86 (1H, m), 3.79 (2H, s), 3.75 (1H, m), 3.07 (1H, t, J=5.5 Hz), 1.82-1.60 (2H, m), 1.07 (3H, t, J=7.5 Hz); ESI-MS m/z 595 (MH⁺).

Example 41

(S)-4-(4-Amino-2-fluorophenoxy)-N-(1-hydroxybutan-2-yl)-7-methoxyquinoline-6-carboxamide (41a)

Similar to the synthesis of compound 1, from compound 39c (300 mg), DMTMM•n-hydrate (329 mg), and (S)-2-aminobutan-1-ol (113 μL), compound 41a was yielded (297 mg, yield: 81%).
¹H-NMR (DMSO-d₆) δ: 8.64 (1H, d, J=5.1 Hz), 8.56 (1H, s), 8.12 (1H, d, J=8.3 Hz), 7.51 (1H, s), 7.09 (1H, t, J=9.0 Hz), 6.56 (1H, dd, J=13.3 Hz, J=2.3 Hz), 6.50-6.43 (2H, m), 5.52 (2H, s), 4.78 (1H, t, J=5.5 Hz), 4.01 (3H, s), 3.95-3.85 (1H, m), 3.56-3.48 (1H, m), 3.46-3.38 (1H, m), 1.74-1.62 (1H, m), 1.54-1.41 (1H, m), 0.93 (3H, t, J=7.4 Hz); ESI-MS m/z 400 (MH⁺).

(S)-4-(2-Fluoro-4-(3-(2-(3-fluorophenyl)acetyl)thioureido)phenoxy)-N-(1-hydroxybutan-2-yl)-7-methoxyquinoline-6-carboxamide (41)

Similar to the synthesis of compound 1d, from compound 41a (100 mg) and 3-fluorophenylacetyl thioisocyanate (73 mg), the titled compound 41 was yielded (115 mg, yield: 78%).
¹H-NMR (DMSO-d₆) δ: 12.44 (1H, s), 11.83 (1H, s), 8.69 (1H, d, J=5.3 Hz), 8.57 (1H, s), 8.13 (1H, d, J=8.3 Hz), 8.03 (1H, d, J=12.2 Hz), 7.59-7.49 (3H, m), 7.44-7.36 (1H, m), 7.23-7.09 (3H, m), 6.52 (1H, d, J=5.3 Hz), 4.77 (1H, t, J=5.5), 4.03 (3H, s), 3.93-3.84 (1H, m), 3.88 (2H, s), 3.54-3.48 (1H, m), 3.45-3.38 (1H, m), 1.72-1.62 (1H, m), 1.54-1.43 (1H, m), 0.93 (3H, t, 7.4 Hz); ESI-MS m/z 595 (MH⁺)

Example 42

4-(4-Amino-2-fluorophenoxy)-N-(2-hydroxy-2-methylpropyl)-7-methoxyquinoline-6-carboxamide (42a)

Similar to the synthesis of compound 1, from compound 39c (103 mg), DMTMM•n-hydrate (104 mg), and 1-amino-2-methylpropan-2-ol (42 mg), compound 42a was yielded (66.3 mg, yield: 53%).

¹H-NMR (400 Hz, CDCl₃) δ: 9.27 (1H, s), 8.64 (1H, d, J=5.2 Hz), 8.26 (1H, sbr), 7.52 (1H, s), 7.02 (1H, dd, J=8.4 Hz), 6.56 (1H, dd, J=12.0 Hz, 2.8 Hz), 6.50 (1H, ddd, J=8.8 Hz, 2.8 Hz, 0.8 Hz), 6.42 (1H, dd, J=5.4 Hz, 1.2 Hz), 4.12 (3H, s), 3.82 (1H, br), 3.57 (2H, d, J=6.0 Hz), 2.70 (1H, sbr), 1.33 (6H, s); ESI-MS m/z 400 (MH⁺)

4-(4-(3-(2-(4-Chlorophenyl)acetyl)thioureido)-2-fluorophenoxy)-N-(2-hydroxy-2-methylpropyl)-7-methoxyquinoline-6-carboxamide (42)

Similar to the synthesis of compound 1d, from compound 42a (55 mg) and 4-chlorophenylacetyl thioisocyanate (43.7 mg), the titled compound 42 was yielded (41.3 mg, yield: 49%).
¹H-NMR (400 Hz, DMSO-d₆) δ:12.45 (1H, s), 11.82 (1H, s), 8.71 (1H, d, J=5.4 Hz), 8.67 (1H, s), 8.35 (1H, t, J=6.1 Hz), 8.02 (1H, d, J=11.0 Hz), 7.58-7.49 (3H, m), 7.43-7.32 (4H, m), 6.55 (1H, d, J=5.4 Hz), 4.04 (3H, s), 3.84 (2H, s), 3.36-3.30 (2H, m), 1.98 (1H, br), 1.15 (6H, s); ESI-MS m/z 611, 613 (MH⁺)

Example 43

(S)-4-(4-(3-(2-(4-Chlorophenyl)acetyl)thioureido)-2-fluorophenoxy)-N-(1-hydroxybutan-2-yl)-7-methoxyquinoline-6-carboxamide (43)

Similar to the synthesis of compound 1d, from compound 41a (63.0 mg) and 4-chlorophenylacetyl thioisocyanate (50.1 mg), the titled compound 43 was yielded (29.9 mg, yield: 31%).
¹H-NMR (400 Hz, CD₃OD) δ: 8.85 (1H, s), 8.63 (1H, d, J=5.6 Hz), 8.07 (1H, dd, J=12.0 Hz, 2.4 Hz), 7.52 (1H, s), 7.50-7.30 (7H, m), 6.60 (1H, dd, J=5.4 Hz, 1.0 Hz), 4.11 (3H, s), 4.08-4.02 (1H, mbr), 3.76 (2H, s), 3.67 (2H, dd, 4.6 Hz), 3.27-3.22 (1H, m), 1.80-1.73 (1H, m), 1.65-1.57 (1H, m), 1.18 (2H, s), 1.04 (3H, t, J=7.6 Hz); ESI-MS m/z 611, 613 (MH⁺)

Example 44

4-(4-(3-(2-(2,6-Difluorophenyl)acetyl)thioureido)-2-fluorophenoxy)-7-methoxyquinoline-6-carboxylic acid (44a)

Similar to the synthesis of compound 1d, from compound 39c (98 mg), 2,6-difluorophenylacetyl thioisocyanate (128 mg), and a solvent mixture of N,N-dimethylacetamide (1.5 mL), toluene (1.5 mL), and ethanol (300 μL), compound 44a was yielded as a crude product (143 mg, yield: 89%).

4-(4-(3-(2-(2,6-Difluorophenyl)acetylthioureido)-2-fluorophenoxy)-7-methoxy-N-(2-morpholinoethyl)quinoline-6-carboxamide (44)

Similar to the synthesis of compound 1, from compound 44a (143 mg), DMTMM•n-hydrate (95 mg), 2-morpholinoethaneamine (51 mg), and N,N-dimethylacetamide (1 mL), the titled compound 44 was yielded (103 mg, yield: 60%).
¹H-NMR (400 Hz, DMSO-d₆) δ: 12.35 (1H, sbr), 11.98 (1H, sbr), 8.70 (1H, d, J=5.3 Hz), 8.70 (1H, s), 8.50 (1H, t, J=5.4 Hz), 8.03 (1H, dbr, J=13.5 Hz), 7.57 (1H, s), 7.61-7.39 (3H, m), 7.18-7.10 (2H, m), 6.53 (1H, d, J=5.3 Hz), 4.07 (3H, s), 3.98 (2H, s), 3.62-3.58 (4H, m), 3.50-3.47 (2H, m), 3.47-3.20 (4H, m), 2.50-2.47 (2H, m); ESI-MS m/z 654 (MH⁺)

Example 45

4-(4-(3-(2-(2,6-Difluorophenyl)acetylthioureido)-2-fluorophenoxy)-N-(2-hydroxy-2-methylpropyl)-7-methoxyquinoline-6-carboxamide (45)

Similar to the synthesis of compound 1, from compound 44a (101 mg), N,N-dimethylacetamide (600 μL), DMTMM•n-hydrate (68 mg), and 1-amino-2-methylpropan-2-ol (31 mg), the titled compound 45 was yielded (74 mg, yield: 65%).
$^1$H-NMR (400 Hz, CDCl$_3$) δ: 12.38 (1H, s), 9.26 (1H, s), 8.69 (1H, sbr), 8.67 (1H, d, J=5.4 Hz), 8.26 (1H, m), 7.97 (1H, dd, J=11.5 Hz, 2.7 Hz), 7.54 (1H, s), 7.43-7.32 (2H, m), 7.04-6.96 (3H, m), 6.44 (1H, dd, J=5.2 Hz, 1, 1 Hz), 4.13 (3H, s), 3.84 (2H, s), 3.57 (2H, d, J=5.9 Hz), 2.58 (1H, s), 1.33 (6H, s); ESI-MS m/z 613 (MH$^+$).

Example 46

4-(4-Amino-2-fluorophenoxy)-7-methoxy-N-methylquinoline-6-carboxamide (46a)

Compound 39b (100 mg) was dissolved in N-methylpiperidin-2-one (250 μL), and 40% methylaminemethanol solution (250 μL) was added thereto, followed by stirring at 40° C. for 16 hours. Subseuqntly, water was added to the reaction mixture, and the precipitate was filtrated, to thereby yield compound 46a (63.7 mg, yield: 64%).
$^1$H-NMR (400 Hz, CDCl$_3$) δ: 9.28 (1H, s), 8.63 (1H, d, J=5.4 Hz), 7.84 (1H, br), 7.50 (1H, s), 7.02 (1H, t, J=8.6 Hz), 6.56 (1H, dd, J=12.0 Hz, 2.4 Hz), 6.50 (1H, ddd, J=8.4 Hz, 2.8 Hz, 0.8 Hz), 6.43 (1H, dd, J=5.2 Hz, 1.2 Hz), 4.11 (3H, s), 3.83, 3.80 (2H, br), 3.08 (3H, d, J=5.0 Hz); ESI-MS m/z 342 (MH$^+$).

4-(2-Fluoro-4-(3-(2-(3-methoxyphenyl)acetyl)thioureido)phenoxy)-7-methoxy-N-methylquinoline-6-carboxamide (46)

Similar to the synthesis of compound 1d, from compound 46a (50.0 mg) and 3-methoxyphenylacetyl isothiocyanate (45.5 mg), the titled compound 46 was yielded (40.1 mg, yield: 50%).
$^1$H-NMR (400 Hz, DMSO-d$_6$) δ: 12.49 (1H, s), 11.79 (1H, s), 8.70 (1H, d, J=5.4 Hz), 8.59 (1H, s), 8.37 (1H, d, J=4.2 Hz), 8.03 (1H, dd, J=12.0 Hz, 2.4 Hz), 7.58-7.49 (3H, m), 7.42-7.33 (2H, m), 7.22-7.17 (2H, m), 6.54 (1H, d, J=4.4 Hz), 4.02 (3H, s), 3.79 (2H, s), 3.75 (3H, s), 2.83 (3H, d, J=4.8 Hz); ESI-MS m/z 549 (MH$^+$)

Example 47

4-(2-Fluoro-4-(3-(2-(4-trifluoromethylphenyl)acetyl)thioureido)phenoxy)-7-methoxy-N-methylquinoline-6-carboxamide (47)

Similar to the synthesis of compound 1d, from compound 46a (50.0 mg) and 4-trifluoromethylphenylacetyl isothiocyanate (53.9 mg), the titled compound 47 was yielded (41.2 mg, yield: 48%).
$^1$H-NMR (400 Hz, DMSO-d$_6$) δ: 12.42 (1H, s), 11.87 (1H, s), 8.69 (1H, d, J=5.2 Hz), 8.59 (1H, s), 8.36 (1H, d, J=4.8 Hz), 8.02 (1H, dd, J=12.0 Hz, 2.0 Hz), 7.72 (2H, d, J=8.4 Hz), 7.60-7.47 (5H, m), 6.52 (1H, d, J=5.2 Hz), 4.02 (3H, s), 3.96 (2H, s), 2.83 (3H, d, J=4.8 Hz) ESI-MS m/z 587 (MH$^+$)

Example 48

Methyl 4-(2-chloro-4-nitrophenoxy)-7-methoxyquinoline-6-carboxylate (48a)

Similar to the synthesis of compound 1a, from methyl 4-chloro-7-methoxyquinoline-6-carboxylate (350 mg), 2-chloro-4-nitrophenol (240 mg), N,N-diisopropylethylamine (484 μL), and N-methylpyrrolidin-2-one (1.5 mL), compound 48a was yielded (130 mg, yield: 24%).
$^1$H-NMR (400 Hz, CDCl$_3$) δ: 8.73 (1H, s), 8.73 (1H, d, J=5.2 Hz), 8.48 (1H, d, J=2.8 Hz), 8.25 (1H, dd, J=8.8 Hz, 2.4 Hz), 7.55 (1H, s), 7.35 (1H, d, J=8.8 Hz), 6.42 (1H, d, J=4.8 Hz), 4.07 (3H, s), 3.98 (3H, s); ESI-MS m/z 389, 391 (MH$^+$)

Methyl 4-(4-amino-2-chlorophenoxy)-7-methoxyquinoline-6-carboxylate (48b)

Similar to the synthesis of compound 1c, from compound 48a (111 mg), a mixture of water-methanol-tetrahydrofuran (1:1:1) (5 mL), iron powder (49.7 mg), and ammonium chloride (111 mg), compound 48b was yielded as a crude product (31.2 mg, yield: 31%). ESI-MS m/z 359, 361 (MH$^+$)

4-(4-Amino-2-chlorophenoxy)-7-methoxy-N-methylquinoline-6-carboxamide (48c)

Similar to the synthesis of compound 46a, from compound 48b (29.0 mg), 40% aqueous methylamine solution (200 μL), and N-methylpyrrolidin-2-one (200 μL), compound 48c was yielded (27.1 mg, yield: 94%).
$^1$H-NMR (400 Hz, CDCl$_3$) δ: 9.30 (1H, s), 8.61 (1H, d, J=5.6 Hz), 7.84 (1H, br), 7.51 (1H, s), 7.02 (1H, d, J=8.4 Hz), 6.83 (1H, d, J=2.8 Hz), 6.64 (1H, dd, J=8.4 Hz, 2.8 Hz), 6.32 (1H, dd, J=5.4 Hz), 4.11 (3H, s), 3.78 (2H, br), 3.08 (3H, d, J=6.0 Hz); ESI-MS m/z 358, 360 (MH$^+$)

4-(2-Chloro-4-(3-(2-phenylacetyl)thioureido)phenoxy)-7-methoxy-N-methylquinoline-6-carboxamide (48)

Similar to the synthesis of compound 1d, from compound 48c (24.0 mg) and phenylacetyl thioisocyanate (17.8 mg), the titled compound 48 was yielded (28.1 mg, yield: 79%).
$^1$H-NMR (400 Hz, DMSO-d$_6$) δ: 12.49 (1H, s), 11.85 (1H, s), 8.94 (1H, d, J=6.0 Hz), 8.69 (1H, s), 8.47 (1H, d, J=4.8 Hz), 8.21 (1H, d, J=1.6 Hz), 7.78 (1H, dd, J=8.6 Hz, 2.0 Hz), 7.61 (1H, d, J=8.8 Hz), 7.59 (1H, s), 7.35-7.13 (5H, m), 6.69 (1H, d, J=5.8 Hz), 4.07 (3H, s), 3.83 (2H, s), 2.84 (3H, d, J=4.4 Hz); ESI-MS m/z 535, 537 (MH$^+$)

Example 49

Methyl 4-(3-fluoro-4-nitrophenoxy)-7-methoxyquinoline-6-carboxylate (49a)

Similar to the synthesis of compound 1a, from methyl 4-chloro-7-methoxyquinoline-6-carboxylate (300 mg), 3-fluoro-4-nitrophenol (225 mg), N,N-diisopropylethylamine (415 μL), and N-methylpyrrolidin-2-one (1.5 mL), compound 49a was yielded (112 mg, yield: 25%).
$^1$H-NMR (400 Hz, DMSO-d$_6$) δ: 8.82 (1H, d, J=5.1 Hz), 8.45 (1H, s), 7.67 (1H, dd, J=12.2 Hz, 2.7 Hz), 7.59 (1H, s), 7.32 (1H, dd, J=8.8 Hz, 2.7 Hz), 6.83-6.74 (1H, m), 3.98 (3H, s), 3.84 (3H, s); ESI-MS m/z 373 (MH$^+$).

Methyl 4-(4-amino-3-fluorophenoxy)-7-methoxyquinoline-6-carboxylate (49b)

Similar to the synthesis of compound 1b, from compound 49a (102 mg), iron powder (76.5 mg), and ammonium chloride (100 mg), compound 49b was yielded (59.7 mg, yield: 64%).

$^1$H-NMR (400 Hz, CDCl$_3$) δ: 8.79 (1H, s), 8.63 (1H, d, J=5.2 Hz), 7.49 (1H, s), 6.91-6.80 (3H, m), 6.44 (1H, d, J=5.2 Hz), 4.05 (3H, s), 3.97 (3H, s), 3.78, 3.75 (2H, br); ESI-MS m/z 343 (MH$^+$)

4-(4-Amino-3-fluorophenoxy)-7-methoxy-N-methylquinoline-6-carboxamide (49c)

Similar to the synthesis of compound 46a, from compound 49b (50.5 mg), 40% aqueous methylamine solution (500 μL), and N-methylpyrrolidin-2-one (500 μL), compound 49c was yielded (31.2 mg, yield: 62%).

$^1$H-NMR (400 Hz, CDCl$_3$) δ: 9.24 (1H, s), 8.62 (1H, d, J=5.6 Hz), 7.86 (1H, sbr), 7.50 (1H, s), 6.90-6.79 (3H, m), 6.46 (1H, d, J=5.2 Hz), 4.11 (3H, s), 3.76, 3.74 (2H, br), 3.08 (3H, d, J=5.0 Hz); ESI-MS m/z 342 (MH$^+$)

4-(3-Fluoro-4-(3-(2-phenylacetyl)thioureido)phenoxy)-7-methoxy-N-methylquinoline-6-carboxamide (49)

Similar to the synthesis of compound 1d, from compound 49c (25.0 mg) and phenylacetyl thioisocyanate (19.5 mg), the titled compound 49 was yielded (13.5 mg, yield: 36%).

$^1$H-NMR (400 Hz, DMSO-d$_6$) δ: 12.51 (1H, s), 11.89 (1H, s), 8.71 (1H, d, J=4.8 Hz), 8.55 (1H, s), 8.34 (1H, d, J=4.8 Hz), 8.06 (1H, dd, J=8.8 Hz), 7.53 (1H, s), 7.42 (1H, dd, J=10.8 Hz, 2.8 Hz), 7.37-7.25 (5H, m), 7.19-7.15 (1H, m), 6.62 (1H, d, J=5.6 Hz), 4.01 (3H, s), 3.83 (2H, s), 2.82 (3H, d, J=4.8 Hz); ESI-MS m/z 519 (MH$^+$)

Example 50

4-(2-Fluoro-4-(3-(2-phenylacetyl)thioureido)phenoxy)-7-methoxy-N,N-dimethylquinoline-6-carboxamide (50)

Similar to the synthesis of compound 1, from compound 1e (285 mg), 50% aqueous dimethylamine solution (147 μL), and DMTMM•n-hydrate (174 mg), the titled compound 50 was yielded (256 mg, yield: 91%).

$^1$H-NMR (400 Hz, DMSO-d$_6$) δ: 12.49 (1H, s), 11.81 (1H, s), 8.66 (1H, dd, J=5.4 Hz, 1.2 Hz), 8.06 (1H, d, J=1.0 Hz), 8.01 (1H, d, J=12.4 Hz), 7.56-7.47 (2H, m), 7.52 (1H, s), 7.38-7.32 (4H, m), 7.31-7.25 (1H, m), 6.52 (1H, d, J=5.1 Hz), 3.97 (3H, d, J=0.8 Hz), 3.83 (2H, s), 3.01 (3H, d, J=1.0 Hz), 2.79 (3H, d, J=1.2 Hz); ESI-MS m/z 533 (MH$^+$)

Example 51

N-(3-Fluoro-4-(7-methoxy-6-(4-(pyrrolidin-1-yl)piperidine-1-carbonyl)quinolin-4-yloxy)phenylcarbamothioyl)-2-phenylacetamide (51)

Similar to the synthesis of compound 1, from compound 1e (27.6 mg), 4-(pyrrolidin-1-yl)piperidine (13.8 mg), and DMTMM•n-hydrate (18.1 mg), the titled compound 51 was yielded (14.1 mg, yield: 39%).

$^1$H-NMR (400 Hz, DMSO-d$_6$) δ: 12.50 (1H, s), 11.83 (1H, s), 8.68 (1H, d, J=5.1 Hz), 8.08 (1H, d, J=14.1), 8.02 (1H, d, J=12.4 Hz), 7.58-7.45 (2H, m), 7.53 (1H, s), 7.40-7.33 (4H, m), 7.33-7.26 (1H, m), 6.53 (1H, dd, J=4.6 Hz), 4.40 (1H, d, J=11.7 Hz), 3.98 (3H, d, J=9.3 Hz), 3.84 (2H, s), 3.10-2.90 (2H, m), 2.75-2.60 (4H, m), 2.05-1.92 (1H, m), 1.85-1.67 (6H, m), 1.55-1.20 (3H, m); ESI-MS m/z 656 (MH$^+$)

Example 52

N-(3-Fluoro-4-(6-(3-hydroxypyrrolidine-1-carbonyl)-7-methoxyquinolin-4-yloxy)phenylcarbamothioyl)-2-phenylacetamide (52)

Similar to the synthesis of compound 1, from compound 1e (20.0 mg), pyrrolidin-3-ol (9.3 mg), and DMTMM•n-hydrate (11.8 mg), the titled compound 52 was yielded (15.0 mg, yield: 71%).

$^1$H-NMR (400 Hz, DMSO-d$_6$) δ: 12.51 (1H, s), 11.85 (1H, s), 8.93 (1H, d, J=6.4 Hz), 8.31 (1H, s), 8.10 (1H, d, J=12.4 Hz), 7.71 (1H, s), 7.61-7.47 (2H, m), 7.40-7.18 (5H, m), 6.87 (1H, d, J=6.1 Hz), 4.33 (1H, br), 4.23 (1H, br), 4.03 (3H, s), 3.83 (2H, s), 2.00-1.80 (4H, m), 1.77-1.72 (2H, m); ESI-MS m/z 575 (MH$^+$)

Comparative Example 1

4-(2-Fluoro-4-(3-(2-phenylacetyl)thioureido)phenoxy)-6,7-dimethoxy-quinoline-6-carboxamide (Comparative Compound 1)

The titled compound was synthesized according to the description of WO 2006/104161.

Test Example 1 c-Met Inhibitory Activity Determination Test (In Vitro)

Inhibitory activity of compounds against c-Met kinase was determined through the following procedures. Method A) c-Met inhibitory assay using AlphaScreen™

A biotinylated peptide including a phosphorylated site of Pyk2 (Tyr402), which is reported as a bio-substrate in Clin. Cancer Res. vol. 8, (2), pp. 620-7 (2002), was employed as a substrate. In the presence of the compound of the present invention, the substrate, c-Met (08-051, Carna bio Co., Ltd), and ATP (final concentration: 20 μM) were added to a reaction buffer (60 mM HEPES (pH: 7.5), 5 mM MgCl$_2$, 5 mM MnCl$_2$, 3 μM Na$_3$VO$_4$, and 1.25 mM DTT). The mixture was allowed to react at room temperature for 20 minutes. EDTA was added to the reaction mixture to a final concentration of 50 mM, to thereby terminate reaction. A detection liquid, which had been prepared by protocol of AlphaScreen™ Phosphotyrosine (P-Tyr-100) Assay Kit (phosphotyrosine-recognizing antibody-bound, 6760620C, Perkin Elmer), was added to the reaction mixture. The reaction was done for one hour at room temperature. Thereafter, the fluorescence intensity from the reaction mixture was measured using a multi-label counter (EnVision™, Perkin Elmer). The compound concentration that realizes 50% inhibition of formation of phosphorylated product was defined as IC$_{50}$ (μM), and the results are shown in the following Tables.

Method B) c-Met Inhibitory Assay Using DeskTop Profiler

A dephosphorylation enzyme inhibitor cocktail (PhosSTOP, #4906837, product of Roche) and a protease inhibitor cocktail (Complete, Mini, EDTA-free, #1836170; product of Roche) were added to a reaction buffer (100 mM HEPES (pH: 7.5), 10 mM MgCl$_2$, 0.003% Brij-35, 0.04% Tween, and 1 mM DTT). In the presence of the compound of the present invention, recombinant c-Met (purified product of Taiho Pharmaceutical Co., Ltd.), fluorescence-labeled c-Met substrate peptide (FL-Peptide 2, #760346, Caliper Life Sciences) (final concentration: 1.5 μM), and ATP (final concentration: 43 μM) were added thereto, and the mixture was allowed to react at 28° C. for 90 minutes. EDTA was added to the reaction mixture to a final concentration of 10 mM, to thereby terminate reaction. By use of DeskTop Profiler (#119900, Caliper Life Sciences), each fluorescence intensity of the substrate and that of the phosphorylated product was determined, whereby the amount of the formed phosphorylated product was determined. The compound concentration that realizes 50% inhibition of formation of phosphorylated product was defined as $IC_{50}$ (μM), and the results are shown in the following Tables.

TABLE 1

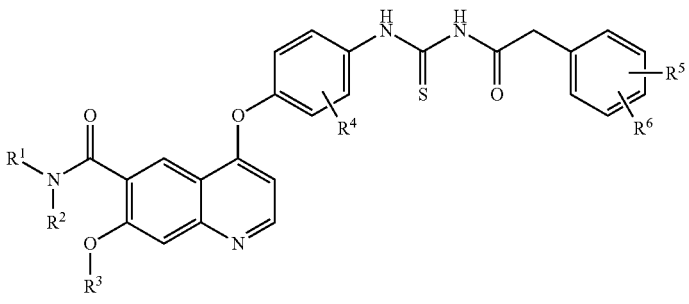

(I)

| Ex. | $R^1$ | $R^2$ | $R^3$ | $R^4$ | $R^5$ | $R^6$ | c-Met $IC_{50}$ (μM) | $IC_{50}$ method |
|---|---|---|---|---|---|---|---|---|
| 1 | H | (CH(CH3)OCH2CH2CH2CH3) | CH3 | 2-F | H | H | 0.210 | A |
| 2 | H | (2,2-dimethyl-1,3-dioxolan-4-yl-ethyl) | CH3 | 2-F | H | H | 0.167 | A |
| 3 | H | (HOCH2CH(OH)CH2CH3) | CH3 | 2-F | H | H | 0.062 | A |
| 4 | H | (3-pyridylethyl) | CH3 | 2-F | H | H | 0.140 | A |
| 5 | H | (1-(2-oxopyrrolidin-1-yl)butyl) | CH3 | 2-F | H | H | 0.116 | A |
| 6 | H | (CH3CH2CH2) | CH3 | 2-F | H | H | 0.104 | A |
| 7 | H | (CH3OCH2CH2CH2) | CH3 | 2-F | H | H | 0.050 | A |
| 8 | H | (Et2NCH2CH2CH2) | CH3 | 2-F | H | H | 0.106 | A |
| 9 | H | (morpholinopropyl) | CH3 | 2-F | H | H | 0.102 | A |
| 10 | H | (HOCH2CH2OCH2CH2CH2) | CH3 | 2-F | H | H | 0.068 | A |

TABLE 1-continued
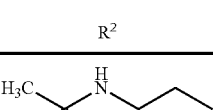
(I)
| Ex. | R¹ | R² | R³ | R⁴ | R⁵ | R⁶ | c-Met IC$_{50}$ (μM) | IC$_{50}$ method |
|---|---|---|---|---|---|---|---|---|
| 11 | H | H₃C-C(O)-NH-propyl | CH3 | 2-F | H | H | 0.145 | A |
| 12 | H | HOCH₂-CH(CH₃)-CH₂OH | CH3 | 2-F | H | H | 0.052 | A |
| 13 | H | BocN-piperidin-4-yl | CH3 | 2-F | H | H | N.D. | A |
| 14 | H | HN-piperidin-4-yl | CH3 | 2-F | H | H | 0.157 | A |
| 15 | H | H₃C-CH₂-NH-C(O)-(4-piperidinyl) | CH3 | 2-F | H | H | 0.138 | A |
| 16 | H | 3-methyl-2-oxoazepan-3-yl | CH3 | 2-F | H | H | 0.177 | A |
| 17 | H | 1-(pyrrolidin-1-yl)propan-1-one-2-yl | CH3 | 2-F | H | H | 0.030 | A |
| 18 | H | 1-acetylpiperidin-4-yl | CH3 | 2-F | H | H | 0.300 | A |
| 19 | H | 3-methyl-2-oxoazepan-3-yl | CH3 | 2-F | H | 4-F | 0.338 | A |

TABLE 2

(I)

| # | R1,R2 (NR1R2 group) | R3 | R4 | R5 | R6 | value | class |
|---|---|---|---|---|---|---|---|
| 20 | H, (S)-3-fluoropyrrolidin-1-yl propanoyl | CH3 | 2-F | H | H | 0.107 | A |
| 21 | H, morpholin-4-yl propanoyl | CH3 | 2-F | H | H | 0.118 | A |
| 22 | H, N,N-dimethyl propanamide | CH3 | 2-F | H | H | 0.250 | A |
| 23 | H, butan-2-ol | CH3 | 2-F | H | 4-F | 0.250 | A |
| 24 | H, 2-methylbutan-2-ol | CH3 | 2-F | H | H | 0.033 | A |
| 25 | H, 4-ethyltetrahydro-2H-pyran-4-ol | CH3 | 2-F | H | H | 0.072 | A |
| 26 | H, 4-ethyltetrahydro-2H-pyran-4-ol | CH3 | 2-F | H | H | 0.125 | A |
| 27 | H, propyl methyl sulfone | CH3 | 2-F | H | H | 0.059 | A |
| 28 | H, 2,3-dimethylphenyl | CH3 | 2-F | H | H | 0.094 | A |

TABLE 2-continued

Structure (I): Quinoline core with R¹R²N-C(O)- at 6-position, R³O- at 7-position, 4-O-linked phenyl (R⁴) attached via -NH-C(S)-NH-C(O)-CH₂- to phenyl (R⁵, R⁶).

| # | R¹ | R² | R³ | R⁴ | R⁵ | R⁶ | IC₅₀ | Class |
|---|----|----|----|----|----|----|------|-------|
| 29 | H | (R)-CH(CH₃)CH₂OH-phenyl (HOCH₂-CH(CH₃)-, with phenyl substituent) | CH3 | 2-F | H | H | 0.234 | A |
| 30 | H | CH₃-N=N-N=C(-)-CH(OH)-CH₂CH₃ | CH3 | 2-F | H | H | 0.040 | A |
| 31 | H | (S)-HOCH₂-CH(CH₃)-CH₂CH₃ | CH3 | 2-F | H | H | 0.026 | B |
| 32 | H | 3-hydroxy-4-methyl-tetrahydrothiophene | CH3 | 2-F | H | H | 0.056 | B |
| 33 | H | CH₃O-CH₂CH₂-NH-C(O)-CH₂CH₃ | CH3 | 2-F | H | H | 0.012 | B |
| 34 | H | (S)-2-(hydroxymethyl)-1-propanoyl-pyrrolidine | CH3 | 2-F | H | H | 0.022 | B |
| 35 | H | (CH₃)₂C(OH)-CH₂-N(CH₂CH₃)-C(O)-CH₂CH₃ | CH3 | 2-F | H | H | 0.031 | B |

TABLE 3

(I)

[Structure of compound I: quinoline with R³O-, R¹R²N-C(=O)-, linked via O to phenyl (R⁴) connected through thiourea (NH-C(=S)-NH) to C(=O)-CH₂-phenyl with R⁵, R⁶ substituents]

| # | R¹ | R² | R³ | R⁴ | R⁵ | R⁶ | | |
|---|----|----|----|----|----|----|----|----|
| 36 | H | N,N-dimethyl-butanamide (H₃C-N(CH₃)-C(=O)-CH₂-CH₂-CH₂-) | CH3 | 2-F | H | H | 0.052 | B |
| 37 | H | morpholinopropyl | CH3 | 2-F | H | 4-F | 0.035 | B |
| 38 | H | (S)-3-hydroxy-2-methylpropyl (H₃C-CH(CH₂-)-CH₂-OH) | CH3 | 2-F | H | 4-F | 0.032 | B |
| 39 | H | 2-hydroxy-2-methylbutyl (H₃C-CH₂-C(CH₃)(OH)-CH₂-) | CH3 | 2-F | H | 2-F | 0.029 | B |
| 40 | H | (S)-3-hydroxy-2-methylpropyl | CH3 | 2-F | H | 2-F | 0.027 | B |
| 41 | H | (S)-3-hydroxy-2-methylpropyl | CH3 | 2-F | H | 3-F | 0.034 | B |
| 42 | H | 2-hydroxy-2-methylbutyl | CH3 | 2-F | H | 4-Cl | 0.045 | B |
| 43 | H | (S)-3-hydroxy-2-methylpropyl | CH3 | 2-F | H | 4-Cl | 0.050 | B |
| 44 | H | morpholinopropyl | CH3 | 2-F | 2-F | 6-F | 0.101 | B |
| 45 | H | 2-hydroxy-2-methylbutyl | CH3 | 2-F | 2-F | 6-F | 0.056 | B |
| 46 | H | ethyl (H₃C-CH₂-) | CH3 | 2-F | H | 3-MeO | 0.085 | B |
| 47 | H | ethyl (H₃C-CH₂-) | CH3 | 2-F | H | 4-CF3 | 0.203 | B |

TABLE 3-continued

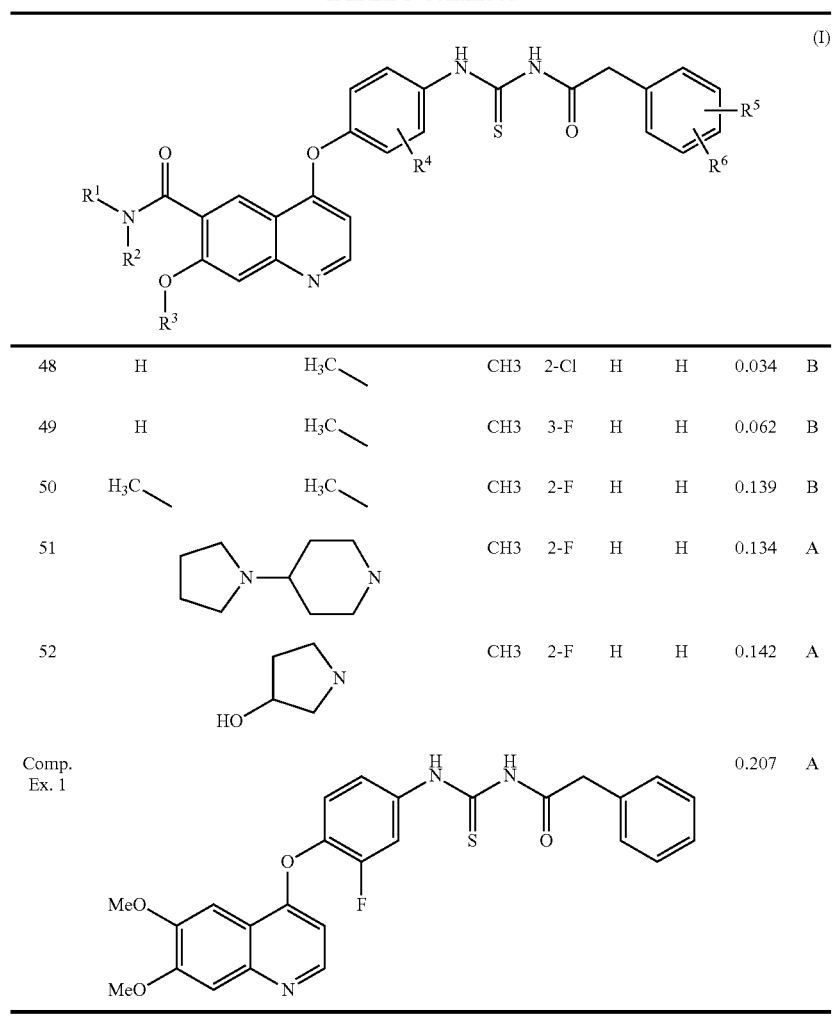

(I)

| | R1 | R2 | R3 | R4 | R5 | R6 | | |
|---|---|---|---|---|---|---|---|---|
| 48 | H | H₃C— | | CH3 | 2-Cl | H | H | 0.034 | B |
| 49 | H | H₃C— | | CH3 | 3-F | H | H | 0.062 | B |
| 50 | H₃C— | H₃C— | | CH3 | 2-F | H | H | 0.139 | B |
| 51 | pyrrolidinyl-piperidinyl | | | CH3 | 2-F | H | H | 0.134 | A |
| 52 | 3-hydroxypyrrolidinyl | | | CH3 | 2-F | H | H | 0.142 | A |
| Comp. Ex. 1 | (structure shown) | | | | | | | 0.207 | A |

A comparative compound (comparative compound 1) was also tested. The comparative compound 1 has a structure similar to that of the compound of the present invention (disclosed in Examples of Patent Document 6) and is known to have utility as a drug (reported in Bioorg. Med. Chem. Lett., 18 (2008), 2793-2798). The test revealed that the compound of the present invention exhibits a c-Met inhibitory activity which is equal to or higher than that of comparative compound 1.

Test Example 2

Cell-Proliferation Inhibitory Assay Against NUGC4 Cells (Human Gastric Cancer Cell Strain in Which c-Met is Over-Expressed and Highly Activated), In Vitro Test NUGC4 cell suspension (in a 10% FBS-containing RPMI 1640 medium (product of Wako Pure Chemical Industries Ltd.) or a FBS-containing DMEM medium (product of Nacalai Tesque, Inc.)) was inoculated to each well of a 96-well (flat-bottom) microplate in an amount of $2\times10^3$ cells (0.1 mL), and the plate was incubated in an incubator under 5% $CO_2$ gas atmosphere at 37° C. for one day. Each of the compounds of the present invention and comparative compound 1 was dissolved in dimethyl sulfoxide to a concentration of 30 mM. The solution was diluted with 10% FBS-containing RPMI 1640 or DMEM medium, to a final test compound concentration of 60, 20, 6, 2, 0.6, or 0.2 µM. The thus-prepared test compound solution was added to each well of the NUGC4 cell culture plate at 0.1 mL/well, and the plate was incubated in an incubator under 5% $CO_2$ gas atmosphere at 37° C. for 3 days. After culturing, 25% aqueous glutaraldehyde solution (product of Nacalai Tesque, Inc.) was added to each well at 20 µL, and the plate was left to stand at room temperature for 20 minutes, whereby cells were fixed. Thereafter, the plate was washed with tap water and dried. Then, aqueous 0.05% Crystal Violet/20% methanol solution (product of Wako Pure Chemical Industries Ltd.) was added to each well at 100 µL/well, and the plate was left to stand at room temperature for 20 minutes, whereby cells were stained. Thereafter, the plate was washed with tap water and dried. To each well, 0.05 M $NaH_2PO_4$/ethanol (1/1=v/v) (100 µL) was added, to thereby extract Crystal Violet. The absorbance of the extracted Crystal Violet was measured at 540 nm using a microplate reader, and the absorbance was employed as an index for living cell count. Percent inhibition was calculated by the following equation, and the 50% inhibition test compound concentration ($IC_{50}$ (µM)) was calculated.

Percent inhibition (%)=$(C-T)/C\times100$

T: Absorbance of well to which a test compound was added
C: Absorbance of well to which no test compound was added

TABLE 4

| | Cell line | | | | | | |
|---|---|---|---|---|---|---|---|
| | NUGC4 | HCT-116 | | HAOSMC | | HMEC | |
| | | | | Type | | | |
| | Cancer | Cancer | | Normal | | Normal | |
| | | | | c-Met status | | | |
| | (+) | (−) | | (−) | | (−) | |
| | IC$_{50}$ (µM) | IC$_{50}$ (µM) | ratio | IC$_{50}$ (µM) | ratio | IC$_{50}$ (µM) | ratio |
| compound 5 | 0.03 | 29 | 857 | >30 | >879 | 23 | 681 |
| compound 15 | 0.02 | >30 | >1584 | >30 | >1584 | >30 | >1584 |
| compound 19 | 0.01 | >30 | >3000 | >30 | >3000 | 18 | 3000 |
| compound 21 | 0.01 | >30 | >3000 | >30 | >3000 | 5 | 3000 |
| compound 22 | 0.01 | >30 | >3000 | >30 | >3000 | >30 | >3000 |
| compound 24 | 0.02 | 23 | 1181 | >30 | >1552 | 16 | 1552 |
| compound 27 | 0.02 | 11 | 714 | >30 | >1893 | 14 | 1894 |
| compound 34 | 0.02 | >30 | >2000 | — | — | — | — |
| compound 37 | 0.01 | >30 | >3000 | — | — | — | — |
| compound 38 | 0.04 | >30 | >719 | — | — | — | — |
| comparative compound 1 | 0.20 | 17 | 82 | 24 | 120 | 15 | 74 |

As apparent from Table 4, the compound of the present invention exhibited cell proliferation inhibitory activity higher than that of comparative compound 1, against NUGC4 (human gastric cancer cell strain in which c-Met is over-expressed and highly activated). Thus, the compound of the present invention has been confirmed to exhibit excellent antitumor activity.

The same in vitro cell proliferation inhibition test was performed against c-Met low expressing tumor cells (HCT-116), normal cells (HAOSMC (human aortic smooth muscle cell)), and normal cells (HMEC (human skin microvascular endothelial cell)). Comparative compound 1 exhibited an IC$_{50}$ of 15 to 24 µM to these cell strains, whereas most of the compounds of the present invention exhibited an IC$_{50}$ of ≧30 µM. Therefore, the compounds of the invention have been confirmed to exhibit a cell proliferation inhibitory activity which is equal to or lower than that of comparative compound 1, against c-Met low expressing cell strains. In other words, as compared with comparative compound 1, the difference (ratio) between IC$_{50}$ of the compound of the present invention against c-Met low expressing cells or normal cells and that against c-Met over-expressing cancer cells is considerably large. Based on this finding, the compound of the present invention has been confirmed to exhibit cell proliferation inhibitory activity with high cell specificity.

Test Example 3

Dose Determination Study for Evaluation of Antitumor Effect (In Vivo)

In order to determine the dose for the evaluation of antitumor effect, each of the compounds of the present invention and comparative compound 1 was perorally administered to nude mice (n=3 to 5/group) for 14 continuous days (once a day). The maximum tolerated dose was calculated based on the change in body weight of the mice.

During the administration period, percent body weight change of mice (BWC %) was calculated. When a ≧10% reduction in mean BWC was observed in a compound-administration group, the dose in that case was determined as a drug-toxicity expression dose. Thus, the half value of the toxicity expression dose was decided as a maximum tolerated dose.

BWC of mice was calculated by the following equation, and the change in mean BWC of each group during the administration period is shown in FIG. 1.

BWC(%)=([(body weight of mouse on the day of weight measurement)−(body weight of mouse at grouping)]/(body weight of mouse at grouping))× 100

As apparent from FIG. 1, no decrease in body weight was observed in the comparative compound 1-administration (100 mg/kg) group during the administration period, but a >10% decrease in BWC was observed in the comparative compound 1-administration (200 mg/kg) group. Thus, the toxicity expression dose of comparative compound 1 was determined as 200 mg/kg, and the maximum tolerated dose was determined as 100 mg/kg. In Test Example 4 (evaluation of antitumor effect), the dose of comparative compound 1 was set to 100 mg/kg.

Meanwhile, no body weight loss was observed in the group administered the compound of the present invention (200 mg/kg). Furthermore, as shown in FIG. 1, no body weight loss was observed in the administration (400 mg/kg) group. Thus, the dose of the compound of the present invention was set to 400 mg/kg in Test Example 4 (evaluation of antitumor effect).

Test Example 4

Evaluation of Antitumor Effect Against Subcutaneously Xenograft Models Using Human Gastric Cancer Strain (NUGC4) (In Vivo)

Human gastric cancer cells (NUGC4) (obtained from ATCC) were subcutaneously transplanted to nude mice. When the tumor volume of tumor-formed nude mice reached about 100 to about 300 mm$^3$, the mice were allocated into groups (5 or 6/group) by stratified randomized allocation such that the mean tumor volumes of each group were equalized (day 1). Each of the compounds of the present invention and comparative compound 1 was perorally administered once a day for 14 continuous days.

Based on the results of Test Example 3, the dose of comparative compound 1 was adjusted to 100 mg/kg/day, which is the maximum tolerated dose during the 14-day administration period of Test Example 4 (i.e., a maximum dose which results in a <10% body weight decrease during the administration period). The dose of the compound of the present invention was adjusted to 400 mg/kg/day.

In order to compare time-dependent changes in tumor proliferation profile among administered test compounds, the relative tumor volume (RTV) in comparison with a tumor volume at the time of allocation was calculated by the following equation. The changes in mean RTV of each group are shown in FIG. 2.

RTV=(tumor volume on the day of tumor volume measurement)/(tumor volume at allocation)

In the case where the mean RTV of an invention compound-administered group on the final evaluation day was smaller than that of the comparative compound 1-administration group and exhibited a statistical significance (Student-t test), the compound of the present invention was found to be significantly more effective than comparative compound 1. In FIG. 2, a statistical significance is marked with *.

Figure 2:
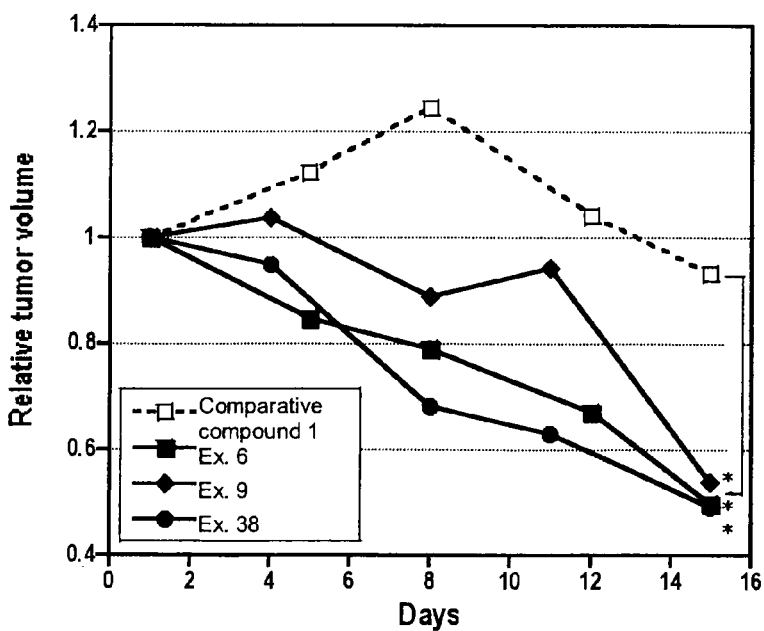
FIG. 2 A graph showing antitumor effects of the compounds of the present invention and of a comparative compound in in vivo tests.

As apparent from FIG. 2, the compound of the present invention induces potent tumor reduction within one week from the start of administration, exhibiting more significant antitumor effect than that of comparative compound 1.

As described hereinabove, the compound of the present invention exhibited a c-Met inhibitory effect which is equal to or higher than that of comparative compound 1 (Test Example 1), and exhibited excellent specificity in cell proliferation inhibitory effect (Test Example 2), indicating that the toxicity to non-targeted cells including normal cells is little. In the dose determination test employing nude mice, the compound of the present invention exhibited no decrease in body weight, even when it was administered at a dose of 400 mg/kg, which is higher than the toxicity expression dose (200 mg/kg) of comparative compound 1, indicating that the compound of the invention had low toxicity (Test Example 3). In addition, the compound of the present invention realized administration at a high dose (400 mg/kg), which is greatly higher than the maximum tolerated dose (100 mg/kg) of comparative compound 1. Thus, the compound of the invention exhibited excellent tumor regression (antitumor effect) (Test Example 4).

The invention claimed is:

1. An acylthiourea compound represented by formula (I):

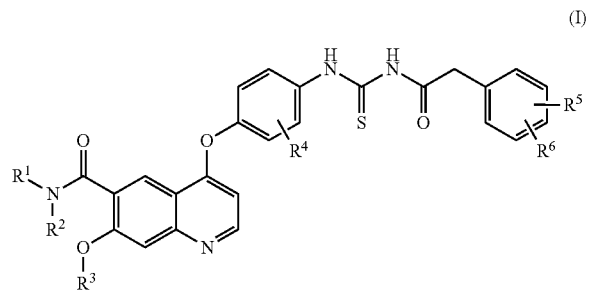

wherein each of $R^1$ and $R^2$, which may be the same or different, represents a hydrogen atom, an optionally substituted $C_{1-6}$ alkyl group, an optionally substituted $C_{3-10}$ cycloalkyl group, an optionally substituted $C_{6-14}$ aromatic hydrocarbon group, or an optionally substituted saturated or unsaturated heterocyclic group, or $R^1$ and $R^2$ may form, together with a nitrogen atom to which they are attached, an optionally substituted nitrogen-containing heterocyclic ring;

$R^3$ represents a $C_{1-6}$ alkyl group; and each of $R^4$, $R^5$, and $R^6$, which may be identical to or different from one another, represents a hydrogen atom, a halogen atom, an optionally substituted $C_{1-6}$ alkyl group, a $C_{1-6}$ alkoxy group, a $C_{1-6}$ alkylamino group, an optionally substituted aromatic hydrocarbon group, or an optionally substituted saturated or unsaturated heterocyclic group, or $R^5$ and $R^6$ may form a ring together with the phenyl ring to which they are attached, or a salt thereof.

2. The acylthiourea compound according to claim 1 or a salt thereof, wherein $R^1$ is a hydrogen atom or a $C_{1-3}$ alkyl group;

$R^2$ is a hydrogen atom, an optionally substituted $C_{1-6}$ alkyl group, an optionally substituted $C_{6-14}$ aromatic hydrocarbon group, or an optionally substituted saturated or unsaturated heterocyclic group, or $R^1$ and $R^2$ may form, together with the nitrogen atom to which they are attached, an optionally substituted saturated nitrogen-containing heterocyclic group;

$R^3$ is a $C_{1-3}$ alkyl group; $R^4$ is a halogen atom; and each of $R^5$ and $R^6$, which are the same or different, is a hydrogen atom, a halogen atom, a $C_{1-3}$ alkyl group which may have a halogen atom as a substituent or $C_{1-3}$ alkoxy group.

3. The acylthiourea compound according to claim 1 or a salt thereof, wherein $R^1$ is a hydrogen atom or a methyl group;

$R^2$ is an optionally substituted $C_{1-6}$ alkyl group, an optionally substituted phenyl group, or an optionally substituted 5- to 7-membered heterocyclic group which has 1 or 2 nitrogen atom(s) or sulfur atom(s), or $R^1$ and $R^2$ form, together with the nitrogen atom to which they are attached, an optionally substituted pyrrolidinyl group or an optionally substituted piperidinyl group;

$R^3$ is a methyl group;

$R^4$ is a fluorine atom or a chlorine atom;

$R^5$ is a hydrogen atom or a halogen atom; and $R^6$ is a hydrogen atom, a halogen atom, a trifluoromethyl group or a methoxy group.

4. The acylthiourea compound according to claim 1 or a salt thereof, wherein $R^1$ is a hydrogen atom;

$R^2$ is a $C_{1-6}$ alkyl group which may have a substituent, said substituent being a hydroxyl group, a $C_{3-10}$ cycloalkyl group, an optionally substituted $C_{1-6}$ alkoxy group, an optionally substituted $C_{1-6}$ alkylamino group, a $C_{1-6}$ alkanoylamino group, a $C_{1-6}$ alkylsulfonyl group, an optionally substituted $C_{6-14}$ aromatic hydrocarbon group, an optionally substituted saturated or unsaturated heterocyclic group, an optionally substituted saturated or unsaturated heterocyclic-carbonyl group, an optionally substituted $C_{1-6}$ alkylaminocarbonyl group, or an optionally substituted saturated or unsaturated heterocyclic-carbonyl group;

$R^3$ is a methyl group;

$R^4$ is a fluorine atom or a chlorine atom;

$R^5$ is a hydrogen atom; and $R^6$ is a hydrogen atom, a fluorine atom, or a chlorine atom.

5. The acylthiourea compound according to claim 1 or a salt thereof, wherein $R^2$ is a $C_{1-4}$ alkyl group which may have a substituent, said substituent being a hydroxyl group, a cyclohexyl group, a $C_{1-3}$ alkoxy group, a $C_{1-6}$ alkylamino group, an acetylamino group, a methylsulfonyl group, a phenyl group, a 5- to 7-membered heterocyclic group having 1 to 4 nitrogen and/or oxygen atom(s), a $C_{1-6}$ alkylaminocarbonyl group, or a 5- to 7-membered heterocyclic-carbonyl group having 1 or 2 nitrogen and/or oxygen atom(s), wherein said $C_{1-3}$ alkoxy group may further have a hydroxyl group as a substituent; said $C_{1-6}$ alkylaminocarbonyl group may further have as a substituent a hydroxyl group or a $C_{1-6}$ alkoxy group; said heterocyclic group may further have as a substituent a $C_{1-6}$ alkyl group or an oxo group; and said heterocyclic-carbonyl group may further have a $C_{1-6}$ alkyl group as a substituent, said $C_{1-6}$ alkyl group optionally having a halogen atom or a hydroxyl group.

6. The acylthiourea compound according to claim 1 or a salt thereof, wherein $R^2$ is a methyl group, an ethyl group, a n-propyl group, an isopropyl group, a n-butyl group, or a sec-butyl group, wherein the substituent of any one of said alkyl groups is a hydroxyl group, a cyclohexyl group, a methoxy group, an ethoxy group, an isopropyloxy group, a diethylamino group, an acetylamino group, a methylsulfonyl group, a phenyl group, a pyrrolidinyl group, a morpholino group, a dioxolanyl group, a tetrahydropyranyl group, a pyridyl group, a triazolyl group, an ethylaminocarbonyl group, a dimethylaminocarbonyl group, a methylbutylaminocarbonyl group, a pyrrolidinylcarbonyl group, or a morpholinocarbonyl group; said alkoxy group may further have a hydroxyl group as a substituent; said heterocyclic group may further have as a substituent a methyl group or an oxo group; said alkylaminocarbonyl group may further have as a substituent a hydroxyl group or a methoxy group; and said heterocyclic-carbonyl group may further have as a substituent a fluorine atom or a methyl group optionally having a hydroxyl group.

7. The acylthiourea compound according to claim 1 or a salt thereof, which is selected from the group consisting of:
- 4-(2-fluoro-4-(3-(2-phenylacetyl)thioureido)phenoxy)-7-methoxy-N-methylquinoline-6-carboxamide;
- 4-(2-fluoro-4-(3-(2-phenylacetyl)thioureido)phenoxy)-7-methoxy-N-(methoxyethyl)quinoline-6-carboxamide;
- 4-(2-fluoro-4-(3-(2-phenylacetyl)thioureido)phenoxy)-7-methoxy-N-(2-morpholinoethyl)quinoline-6-carboxamide;
- 4-(2-fluoro-4-(3-(2-phenylacetyl)thioureido)phenoxy)-7-methoxy-N-(2-morpholino-2-oxoethyl)quinoline-6-carboxamide;
- 4-(2-fluoro-4-(3-(2-(4-fluorophenyl)acetyl)thioureido)phenoxy)-N-(2-hydroxybutyl)-7-methoxyquinoline-6-carboxamide;
- 4-(2-fluoro-4-(3-(2-phenylacetyl)thioureido)phenoxy)-N-(2-hydroxy-2-methylpropyl)-7-methoxyquinoline-6-carboxamide;
- (S)-4-(2-fluoro-4-(3-(2-phenylacetyl)thioureido)phenoxy)-N-(1-hydroxybutan-2-yl)-7-methoxyquinoline-6-carboxamide;
- 4-(2-fluoro-4-(3-(2-(4-fluorophenyl)acetyl)thioureido)phenoxy)-7-methoxy-N-(2-morpholinoethyl)quinoline-6-carboxamide;
- (S)-4-(2-fluoro-4-(3-(2-(4-fluorophenyl)acetyl)thioureido)phenoxy)-N-(1-hydroxybutan-2-yl)-7-methoxyquinoline-6-carboxamide;
- (S)-4-(2-fluoro-4-(3-(2-(2-fluorophenyl)acetyl)thioureido)phenoxy)-N-(1-hydroxybutan-2-yl)-7-methoxyquinoline-6-carboxamide; and
- (S)-4-(4-(3-(2-(4-chlorophenyl)acetyl)thioureido)-2-fluorophenoxy)-N-(1-hydroxybutan-2-yl)-7-methoxyquinoline-6-carboxamide.

8. A pharmaceutical agent, comprising, as an active ingredient, the acylthiourea compound according to any one of claims 1 to 7 or a salt thereof.

9. An antitumor agent, comprising, as an active ingredient, the acylthiourea compound according to any one of claims 1 to 7 or a salt thereof.

10. A pharmaceutical composition, comprising:
the acylthiourea compound according to any one of claims 1 to 7 or a salt thereof; and
a pharmaceutically acceptable carrier.

11. A method of producing an antitumor agent, the method comprising:
combining the acylthiourea compound according to any one of claims 1 to 7 or a salt thereof, with a pharmaceutically acceptable carrier.

12. A method for treatment of a tumor, the method comprising:
administering to a subject in need thereof, an effective amount of the acylthiourea compound according to any one of claims 1 to 7 or a salt thereof.

* * * * *